United States Patent [19]
Nelson et al.

[11] Patent Number: 5,999,836
[45] Date of Patent: *Dec. 7, 1999

[54] ENHANCED HIGH RESOLUTION BREAST IMAGING DEVICE AND METHOD UTILIZING NON-IONIZING RADIATION OF NARROW SPECTRAL BANDWIDTH

[76] Inventors: Robert S. Nelson, 2922 Upshur St., San Diego, Calif. 92106; Reuven D. Zach, 1039 N. Harper Ave., #8, Los Angeles, Calif. 90046

[ * ] Notice: This patent issued on a continued prosecution application filed under 37 CFR 1.53(d), and is subject to the twenty year patent term provisions of 35 U.S.C. 154(a)(2).

[21] Appl. No.: 08/597,447

[22] Filed: Feb. 2, 1996

Related U.S. Application Data

[63] Continuation-in-part of application No. 08/480,760, Jun. 6, 1995, abandoned.

[51] Int. Cl.$^6$ ........................ A61B 5/00
[52] U.S. Cl. ............ 600/407; 600/425; 600/473; 600/476; 250/339.02; 250/341.1; 250/341.7; 250/358.1; 250/360.1
[58] Field of Search ............. 600/425, 427, 600/443, 448, 459, 476, 473, 407; 250/341.1, 341.7, 339.02, 358.1, 360.1

[56] References Cited

U.S. PATENT DOCUMENTS 4,433,690  2/1984  Green et al. .................... 600/448
4,767,928  8/1988  Nelson et al. .................. 600/425

Primary Examiner—Ruth S. Smith
Attorney, Agent, or Firm—Lyon & Lyon LLP

[57] ABSTRACT

The present invention provides a method and apparatus for high resolution breast imaging using collimated non-ionizing acoustic radiation and electromagnetic radiation in the near ultraviolet, visible, infrared and microwave regions (i.e. "light") rather than ionizing x-radiation. The light used is of a narrow spectral bandwidth in that the optical properties of interest are relatively uniform over the bandwidth. The incident collimated light is transmitted through and backscattered out of a breast. Normal and diseased breast materials exhibit comparatively distinct characteristics when exposed to radiation and are thereby differentiated. Collimation can also be used to control the level of scattered radiation. Radiation coupling materials can be employed during image acquisition to enhance radiation coupling into and out of the breast as well as providing desirable absorption and scattering properties. Additional scatter reduction and/or improved sensitivity can be attained by compressing a region of the breast using contoured and/or flat compression plates of various sizes which may include an open region allowing access to the surface of the breast for irradiating a portion of the breast. An acoustic field can be introduced into a volume of breast tissue altering its optical qualities. These changes can be recorded by intersecting an optical field with the acoustic field, providing spatial information and tissue characterization.

29 Claims, 16 Drawing Sheets

RASTER SCAN FORMAT INCIDENT
NORMAL TO SURFACE

MULTIPLE RASTER SCAN

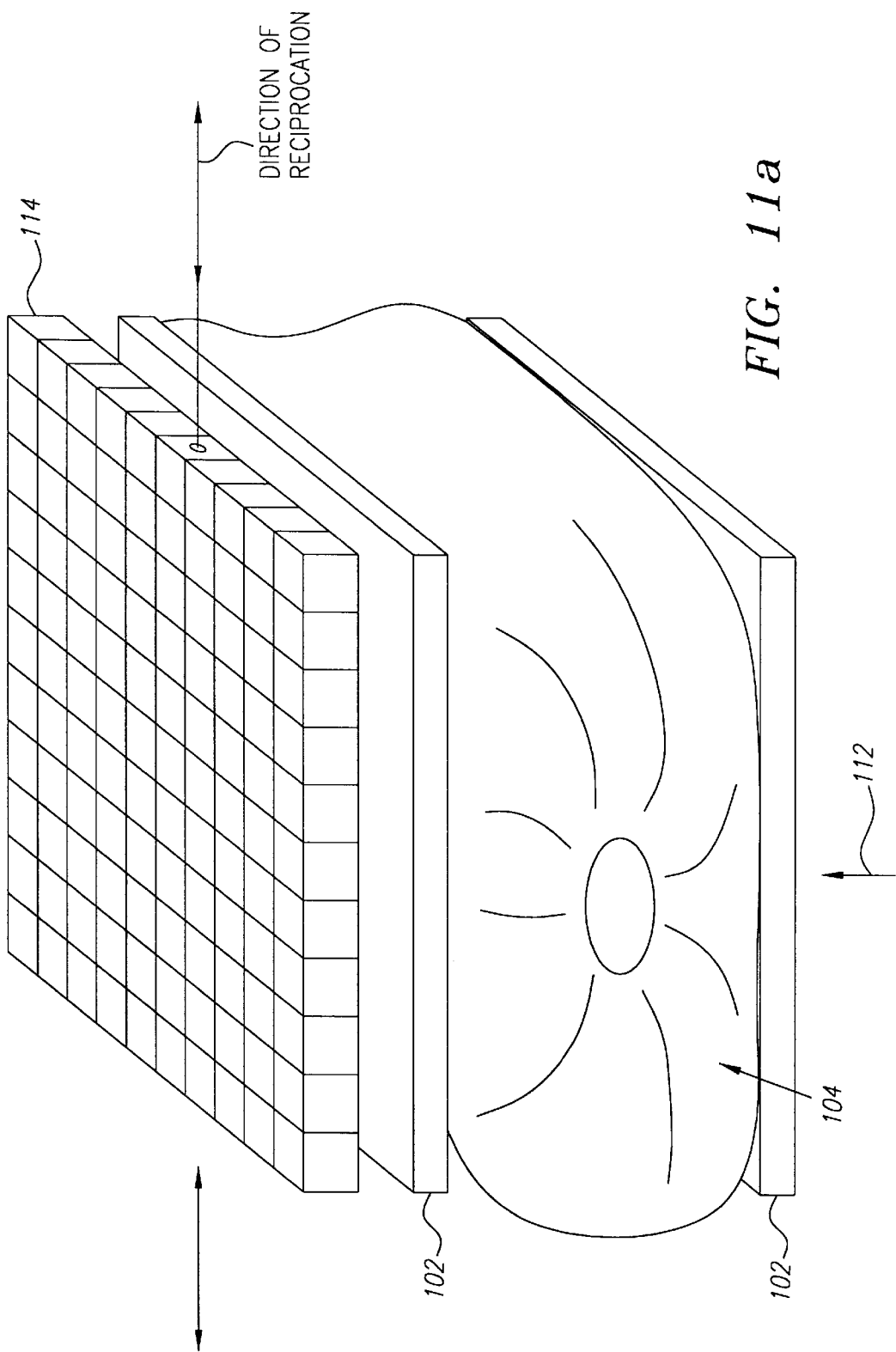

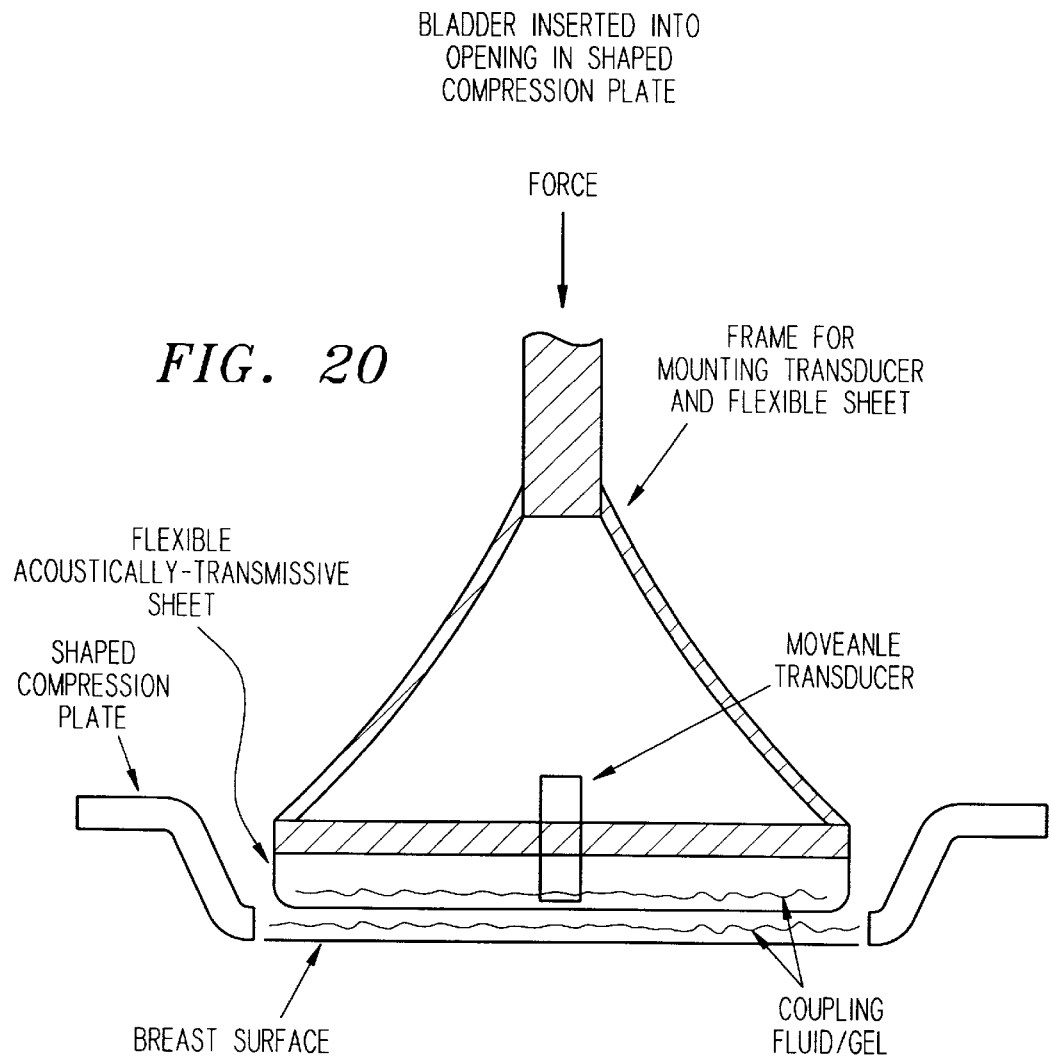

ENHANCED HIGH RESOLUTION BREAST IMAGING DEVICE AND METHOD UTILIZING NON-IONIZING RADIATION OF NARROW SPECTRAL BANDWIDTH

RELATED APPLICATION INFORMATION

This application is a continuation in part of application Ser. No. 08/480,760, filed Jun. 6, 1995, now abandoned the disclosure of which is hereby incorporated by reference as if fully set forth herein.

FIELD OF THE INVENTION

The present invention relates to breast imaging devices and methods using non-ionizing radiation of narrow spectral bandwidth, particularly, enhancing the images obtained by such devices and methods.

BACKGROUND OF THE INVENTION

The present invention can be understood more fully if image enhancement techniques developed for x-ray radiography (and in particular x-ray mammography) are detailed first.

Two aspects of traditional radiographic x-ray imaging, spectrum optimization and scatter rejection (or reduction), are of particular concern in specialized fields such as mammography and angiography. A variety of point, slit, and slot scanning systems have been designed to optimize the spectrum and scatter reduction, and special filters have been employed to shape the source spectrum for both mammography and angiography. See, R. Nelson, Dissertation, "High Resolution Slit Scan Techniques for Digital Radiography", Department of Radiological Sciences, University of California, Los Angeles (1986). For example, in the case of dual-energy k-edge subtraction angiography, the desire for a very narrow bandwidth intense x-ray beam resulted in the replacement of a conventional x-ray tube source with an approximation to a pulsed x-ray laser source: a synchrotron. E. Rubenstein, et al., SPIE vol. 314, Digital Radiography (Sept. 14–16, 1981). The use of a highly directional, narrow bandwidth, slit scanning beam from a synchrotron (a source of potentially very short pulses on the order of tens of picoseconds, see N. Schwentner, et al., Nuclear Instruments and Methods vol. 167, p.499–503 (1979)) presented opportunities to achieve additional scatter reduction.

Although it is difficult to exploit radiation beam properties such as polarization and coherence for scatter reduction at radiographic energies (typically above 15 Kev), it is possible to consider employing energy—selective, angle-selective, and time-of-flight (TOF) methods to limit large angle scatter and small angle scatter contributions (including contributions from multiple-scattered photons which emerge with a direction vector similar to that of the unscattered transmitted beam) to the image spatial contrast resolution and signal-to-noise ratio (SNR). The importance of utilizing all three methods in an imaging system has been understood by researchers in the field of positron emission tomography. See J. Llacer, et al., 1 IEEE Trans. Nucl. Sci. NS-20, p. 282–293 (1973). In addition, the principle of TOF has been exploited in the field of medical ultrasound for many years.

Mechanisms which can provide additional scatter rejection in a radiographic imaging system can be used either to enhance the image contrast resolution or alternatively to allow expansion of the beam size from a slit to a slot or area beam (thereby reducing image acquisition time) while maintaining an acceptable level of image contrast resolution. Unfortunately, implementing energy-selective x-ray spectroscopy with a detector array experiencing very high count rates is difficult and compromises may be required. See Nelson, et al., U.S. Pat. No. 4,937,453 (1990).

Implementing a TOF imaging system by gating or modulating an array of x-ray detectors which are designed to provide high contrast resolution and efficiency represents another challenging problem. Of course, additional scatter reduction is still possible if low-tech concepts are implemented. For example, an inexpensive spatial filter such as a focused x-ray grid could be added to remove some fraction of the large angle x-ray scatter in the plane of the slit.

Clinical x-ray mammography, which employs a film-screen receptor and a molybdenum-anode x-ray tube, is currently used as a mass-screening technique for breast disease. Two views of a breast are usually acquired in order to help separate overlapping objects, providing a very simple form of tomography. However, certain risks are associated with x-ray examinations since x-ray radiation is also ionizing, and, therefore, the exposure to which should be minimized. Minimizing exposure equates to limiting the frequency and number of exams and limiting exams to patients having a minimum recommended age. Conventional and unconventional (including CT and stereotactic) imaging techniques have been developed for x-ray mammography with the goals of improving image contrast resolution and improving detection of disease while lowering patient risk and exposure.

In x-ray mammography it is desirable to use a range of x-ray (electromagnetic) energies that will enhance the radiologists' ability to differentiate normal from diseased tissue while limiting patient radiation dose to tolerable levels. Unfortunately, in general, the use of such an x-ray energy range results in scattered x-ray photons comprising a significant fraction of the transmitted beam. Additional problems can arise due to the energy-dependent filtering action of a breast when a broad band mammography x-ray source is used (i.e. beam hardening). Both x-ray scatter and beam hardening problems can be reduced by compressing the breast to be imaged (which also helps reduce patient motion problems) while additional scatter reduction can be obtained by using an air gap and a focused x-ray grid (collimator). If the breast is sufficiently compressed, a focused grid need not be used at all. Both the air gap and the focused grid function as spatial filters, although the angular selectivity of the grid is relatively poor compared to what can be implemented in the optical realm (due in part to the energy range in which the grid is used and the angular distribution of the unfocused x-ray source). The size of the air gap cannot be too large due to magnification effects. The use of air gaps and grids represent conventional, widely practiced methods for improving image quality when a broad energy bandwidth relatively large area x-ray beam is used in clinical mammography.

The use of (preferably) narrow bandwidth, time-resolved or TOF imaging systems in x-ray mammography in a clinical setting is still impractical due to the lack of an affordable sufficiently brilliant pulsed source (synchrotrons are relatively expensive) and the lack of an inexpensive gated detector capable of high contrast resolution and efficiency (film-screen receptors are not sufficient and are still dominant in clinical mammography). Rationalizing the use of such expensive equipment to lower the cost of an expensive angiographic procedure is far easier than rationalizing the same for mammography, a mass-screening examination which is relatively inexpensive. If a TOF system could be implemented for x-ray mammography then a primary limitation on acquisition time (other than exposure to x-rays) is patient motion, i.e. the image or image segment must be acquired before patient motion affects the image and thereby becomes a problem. The integrated x-ray fluence requirements will be the same whether integration is over one intense short pulse or a rapid sequence of many weak short pulses. The power per pulse (for a single intense pulse or a rapid sequence of weak pulses) is not likely to be of concern at mammography x-ray energies since a tolerable fraction of unscattered photons are transmitted for the case of a typical compressed breast. Contrast this with TOF optical mammography imaging problems. In the case of TOF optical imaging attempts to image the unscattered component of the optical beam transmitted through a typical compressed breast, within the time constraints imposed by patient motion, could pose a radiation safety risk (e.g. burns).

Although a cost-effective, narrow bandwidth TOF x-ray mammography system is not available, it is still desirable to implement optimized beam filtration and scatter reduction techniques. A common approach to limiting transmitted scatter is to reduce the area of the x-ray beam. Given time constraints for image acquisition (patient motion and exposure) and limitations on the heat or electrical current capacity of the x-ray tube as well as the tube focal spot distribution, a slit or slot scanning format may be acceptable. Ideally, the size of the slit or slot would be appropriate for the thickness (and material composition) of the breast being imaged. The range of x-ray energies commonly used in film-screen mammography primarily exhibit two scattering mechanisms: Rayleigh or coherent scattering (elastic scattering without energy loss) and Compton scattering (inelastic scattering). See Radiologic Health Handbook p. 133 and 438, U.S. Department of Health, Education, and Welfare (January 1970); and see W. Veigele, Atomic Data Tables Vol. 5, p. 51–111 (1973) (for coherent and incoherent scatter cross-sections for hydrogen, carbon, nitrogen and oxygen see pages 66–69). For the range of energies used in x-ray mammography coherent scatter can comprise a significant fraction of the total scatter component of the transmitted x-ray beam reaching the detector. The affect on the resultant image appears to be a reduction of contrast and SNR. See P. Johns, et al., Med. Phys. 10(1), p. 40–50 (1983); and H. Barrett, et al., Radiological Imaging, vol. II, p. 631–635 (1981) (scatter point spread function). It should be noted that Rayleigh scattering is the primary concern when using visible and near-infrared wavelengths. See A. Ishimaru, Wave Propagation and Scattering in Random Media, vol. 1, p. 18 (1978). The Rayleigh or coherent component of x-ray scatter is typically small-angle scatter (although the coherent scatter peaks at an angle which appears to be much larger for x-ray mammography than for optical mammography).

An x-ray mammography TOF technique would ideally allow separation of unscattered x-ray photons from scattered x-ray photons (i.e. small angle scattered and large angle scattered (including multiple scattered x-ray photons which exit from the breast aligned with the unscattered beam)). Breast compression would still be very desirable because the contribution to the detected signal from the unscattered component is diminished exponentially with increasing breast thickness. A compressed breast or breast region also ensures that the tissue volume being imaged is of uniform thickness. A uniform thickness reduces the need for an extremely large detector dynamic range (which is a problem for mammography film-screen detection systems) and timing difficulties related to initiating gating in a TOF system. Image degradation from x-ray scatter remains a problem for clinical x-ray mammography imaging systems. Small angle scattered x-rays degrade the desired image far less than large angle scattered x-rays. In addition, the information content of small angle scattered x-rays could be potentially useful since these x-rays may sample a tissue volume which is similar to the desired tissue volume. The information content of small angle scatter x-ray can be enhanced if the tissue volume which can be sampled by all or part of the detected beam is restricted (for example by compressing the breast or limiting the size of the incident x-ray beam).

A perceived advantage of a TOF technique can be added to an x-ray mammography system design if large angle scatter (which is primarily Compton scatter) propagating approximately along the unscattered x-ray beam direction can be removed. This can be accomplished in part if a narrow bandwidth directional source is used, if a detection system offers energy-dependent directional discrimination capabilities, and if the beam-aligned Compton scattered photons have lost sufficient energy to be rejected by the detector. At mammography x-ray energies this condition is most likely to occur if photons undergo multiple Compton scattering. See H. Barrett, et al., Radiological Imaging vol. I, p. 321 (1981). The energy-dependent directional discrimination capability of the detector can also be used to remove part of the Compton or the Rayleigh scatter component which emerges from the breast with too large an angle with respect to the unscattered beam direction. See Nelson, et al., U.S. Pat. No. 4,958,368; and Nelson, et al., U.S. Pat. No. 4,969,175. If energy discrimination is not available, then spatially limiting the size of the x-ray beam becomes more important since this reduces the x-ray cross-talk contribution from adjacent tissue volumes to the unscattered x-ray photon beam exiting the breast.

Before leaving the topic of x-ray radiography it is useful to review additional x-ray imaging techniques capable of providing three dimensional information. In one case x-ray fluorescence was used to measure iodine concentration in thyroids. See H. Barrett, et al. Radiological Imaging vol. II, p. 661–662, (1981). Computed tomography (CT) enhances the available data set by acquiring projections from many directions, permitting three dimensional information to be synthesized from two dimensional data sets. Tomography, the poor-mans' CT, provides an image of a specific layer of a body part with (preferably) minimum distortion from the surrounding layers. Recently classical film-based tomography has been modified to include a digital acquisition system. Data from multiple angled projections can be combined to synthesize (by tomosynthesis) a three dimensional image. See H. Barret, et al., Radiological Imaging, Vol. 2, p. 368–370 (1981). Also see D. Nishimura, et al., SPIE vol. 314, Digital Radiography, p. 31–36 (1981); and J. Liu, et al., IEEE Trans Medical Imaging, Vol. 8, No. 2, p. 168–172, 1989). Although scatter reduction is considered desirable for typical transmission radiography applications, there are many techniques where x-ray scatter, including backscatter, has been used for imaging and densitometry. See J. Battista, et al., Phys. Med. Biol., vol. 22(2), p. 229–244 (1977); and (A. Jacobs, et al., SPIE vol. 206, p. 129–134 (1979) (backscatter imaging). Given the right conditions at least a fraction of the scattered x-rays can carry useful information.

The ability to limit the level of photon scatter and photon scatter distribution in a detected beam is important for optical mammography imaging as well as x-ray mammography. In optical mammography the maximum breast thickness for which a transmitted signal resulting from unscattered photons can be detected is dramatically less than for x-ray mammography. This implies that for a typical compressed breast there is little benefit gained from using optical photon pulses which are shorter than some minimum temporal width since practically all of the optical photons exiting along the desired direction are scattered. This does, not mean, however, that a TOF technique utilizing only unscattered photons could not be used for a sufficiently thin subject. See M. Duguay, et al., Applied Optics, vol. 10, No. 9, p. 2162–2170 (1971). The scale of this unscattered optical photon beam problem is readily apparent if one considers the work of early researchers concerned with optical propagation in blood, in particular the scatter cross-section and the mean cosine of the forward scatter component as a function of wavelength. See C. Johnson, IEEE Trans. Bio-Medical Engineering, vol. BME-17, No. 2, p. 129–133 (1970); and G. Pedersen, et al., Biophysical Journal, vol. 16, p. 199–207 (1976). As is the case for x-ray mammography, beyond some thickness of breast in order to generate a desired image (with adequate photon statistics) using optical photons with "optimal" information content the amount of energy absorbed by the breast being imaged becomes unacceptable. The imaging technique must be modified. In conventional x-ray mammography the x-ray tube potential might be increased and the x-ray receptor could be changed (e.g., Xeromammography). The compromise involves imaging with x-ray photons energies which will provide less than optimal information content (about absorption in tissue) in exchange for an acceptable patient dose.

For optical mammography imaging a modified TOF technique could be used to limit contributions from scattered photons which have sampled tissue outside the tissue volume of interest. The objective is to try to maximize the relevant information content of the imaged scattered photons which could help characterize the tissue volume which is being examined. See J. Maarek, et al., Med. & Bio. Eng'g & Com., p. 407–413 (July 1986). The drawback of allowing a longer flight time for photons is that the distribution of possible paths for the imaged photons and the acceptable angular distribution of the exiting imaged photons also increases. Unfortunately, in the optical case, the capability to filter photons which follow inappropriate paths is minimal (i.e., there is minimal spectral discrimination). Undesirable scatter contributions can be reduced by spatially limiting the size of the optical beam and using collimation which provides angular selectivity (which is also implemented in x-ray mammography).

Another problem for optical mammography imaging is that entrance and exit surfaces of the object to be imaged (i.e., skin surfaces) are typically not smooth. Optical photons can be greatly affected by the surface structure of the skin whereas x-ray photons are relatively insensitive to skin surface conditions. An optical coupling fluid or gel can help reduce the effects of an irregular skin surface. See U.S. Pat. Appln. Ser. No. 08/480,760, filed June 1995. Optical properties such as polarization (which is relatively impractical to utilize in x-ray mammography) may also be exploited. The ability to reduce degrading effects of optical scatter can be of benefit for other time-resolved techniques and is not limited to the TOF approach.

In recent years, broad beam light sources (sometimes referred to as "light torches") having a relatively wide spectral bandwidth in the visible and near-infrared range have been used for breast imaging. Broad beam light transmitted through a breast is typically recorded by a video camera and viewed on a video monitor or analyzed by a computer. However, the ability to discriminate between various types of tissue in a breast via this technique is reduced since the transmitted beam has a wide spectral bandwidth and the captured radiation is largely comprised of scattered radiation (i.e. contrast is lost). Light may be absorbed, transmitted, scattered, and reflected to different degrees by various types of tissue making it difficult to extract information about the nature of any tissue. Detection limits for this technique have generally been restricted to lesions which are no smaller than what a physician can detect by palpitation. Therefore, this technique is not particularly advantageous and has fallen out of favor in the United States.

As the present applicants described in now issued U.S. Pat. Nos. 4,649,275, 4,767,928, 4,829,184, 4,948,974, and pending patent application Ser. No. 08/480,760, filed Jun. 6, 1995, a collimated (i.e. focused) continuous wave (CW) or rapidly pulsed light (i.e. non-ionizing electromagnetic radiation including near-ultraviolet, visible, infrared, microwave, etc.) source of narrow spectral bandwidth (such as is generated by a filter lamp, LED, laser, a waveguide, a phased array, etc.) can be used to produce a beam or a number of beams of light having relatively small spatial dimensions appropriate for acquiring images of a breast with high spatial contrast resolution. The narrow spectral bandwidth of the beam, along with other beam parameters (such as polarization, directional qualities or angular distribution, etc.) enable improved characterization of the composition of the breast material being imaged. Additional information can be obtained by acquiring images at other wavelengths with narrow spectral bandwidths (and/or other modifications to beam parameters).

For transmission imaging it is preferred that the light source be positioned on one side of the breast and a receiver, such as a photodetector (radiation detector), be positioned on the opposite side to record transmitted light. For back-scatter imaging the photodetector will be on the same side of the breast as the source. As is shown in FIGS. 1 and 2, in many instances it is preferred that the breast be compressed between compression plates, flattening (or shaping) the entrance and/or exit surface(s) while reducing the typical distance the radiation must travel before exiting the breast and being detected. An additional benefit is that the region being imaged tends to be of a more uniform thickness when compression plates are employed.

The type of optical (radiation) source (CW, modulated CW, pulsed, etc.), as well as other possible properties such as beam coherence, wavefront phase, polarization, angular and spectral distribution (the source may be tuneable), are altered by absorption and scattering as the beam propagates through the breast and plates. The radiation exiting the breast can be analyzed using various forms of external collimation such as air gaps, focused lenses (single lenses, lens combinations, holographic or diffractive lenses, etc.), narrow spectral bandwidth filters, directionally-sensitive filters, narrow spectral bandwidth and directionally-sensitive filters (for example, multilayer films, interferometers, etc.), polarized filters, amplifiers (including nonlinear amplifiers), optical shutters and mechanical apertures, holographic or diffractive spatial filters as well as acousto-optic devices which exhibit high angular sensitivity, fiber optics and amplified fiber optics, light pipes, waveguides, masks, focused arrays, etc.

Image resolution can be influenced by adjusting the cross-sectional area of the optical beam(s). The advantage of using a radiation beam of relatively small dimensions (either its two dimensional area cross-section which is typically defined as being normal to the beam axis or three dimensional volume cross-section in the case of a short pulse or a source with a short coherence length) is the ability to limit single and multiple scatter cross-talk contributions to the measured signal from neighboring tissue volumes. A number of factors such as the thickness of tissue, the uniformity of the region being imaged, the scatter reduction mechanisms employed, whether a time-resolved or diffusive-wave optical technique is implemented, etc., influence acceptable beam dimensions. For example, in a practical imaging system, there are almost no unscattered (ballistic) photons for thicknesses of breast tissue greater than a few centimeters. The ability to exploit minimally scattered photons (the snake component) and extend the acceptable range of tissue thickness is limited. The implication is that the utilization of breast compression is highly advantageous when making use of the snake component when imaging a typical breast. An additional drawback is the increased cross-talk within the beam relative to what can be achieved with a time-resolved technique (such as TOF) which successfully records only ballistic photons. Thus, if the snake component is utilized for optical imaging it is beneficial to use a smaller beam cross-section in comparison to the case in which optical imaging involves only the ballistic component.

The electromagnetic properties of various normal and diseased breast tissues may exhibit wavelength dependence. Thus, acquiring images at different wavelengths of light as well as examining the effects of tissue on other electromagnetic parameters (e.g., direction vector, polarization, phase, amplitude, temporal profile, coherence, etc.) may aid in distinguishing between various types of tissue. High resolution images may be obtained with a variety of scanning techniques: FIGS. 2a and 2b show a point beam or multiple point beam which can be used in a raster scan format. The transmitted light beam can be collimated by a variety of means. This approach can be extended to include a single line or multiple line scan format as shown in FIG. 2c. High speed two-dimensional imaging is shown in FIG. 2d. In this case collimation (such as fiber-optics or light pipes) can be introduced into one or both compression plates. FIG. 3 shows a (patterned) mask collimator which can be used to generate multiple beams. In all cases collimation may be used to produce a beam or beams of relatively small cross-section and directional nature. These attributes can be used to help exclude unwanted scatter in the detected beam.

If two or more sources providing light beams of differing wavelengths (i.e., $\lambda_1$ and $\lambda_2$) are spatially separated as shown in FIG. 1b, then narrow spectral bandwidth filters can be used between plate B and the detectors for each wavelength such that the detector for $\lambda_2$ rejects light of wavelength $\lambda_1$ which is scattered into the path of the $\lambda_2$ beam. In this case the spectral filter functions as a collimator, rejecting a component of the transmitted beam which can only be attributed to scatter. By positioning source 1 (for $\lambda_1$) adjacent to source 2 (for $\lambda_2$) the scatter contribution from source 1 into itself (near the boundary with source 2) can be estimated by measuring the $\lambda_2$ component at the location of source 1. This assumes that radiation of wavelengths $\lambda_1$ and $\lambda_2$ have similar scattering and absorption properties for the type of tissue being imaged. Another technique is to have sources 1 and 2 incident at the same location, but source 2 would be tilted with respect to source 1. If source 1 and source 2 have the same properties, then source 2 should be pulsed at a distinctly separate time relative to source 1 being pulsed (use a temporal offset) to help minimize beam cross-talk. The source 2 component measured at the location of the source 1 detector can be used to estimate a scatter correction in some instances. This measurement could, taking a different perspective, also be attributed to a new (virtual) beam which was created at a greater effective depth than source 1.

Thus, one approach to estimating scatter corrections or contributions is to use two sources with different wavelengths. Another technique is to use two sources with different polarizations (or simply alter the polarization of a single source) and acquire two measurements at different times. The source 1 detector can be used as a second detector or a separate detector can be employed. If a beam splitter can be used to separate the exiting beam (transmitted and/or backscattered) into two parts (or separate the exiting beam components directly) then two detectors can be used to make simultaneous measurements of the beam components.

Optical (non-ionizing radiation) tomography utilizing a collimator can be employed in a variety of fashions. For example, as shown in FIG. 6, an object, such as a breast 30 may be imaged by a source of radiation 32 generating a one or two dimensional radiation beam, a detector 34, and a collimator 36 disposed between the source 32 and the detector 34. In this way multiple two dimensional images may be obtained simultaneously, thereby providing a three dimensional image of the object. For example, as shown in FIG. 7, a line source 42 or linear array of point sources may irradiate the object to be scanned such as a breast 44. Transmitted radiation then passes through a collimator 46, and then is detected by a detector 48, such as a two dimensional array of detectors, or a camera. FIG. 11b shows an arrangement similar to that shown in FIG. 7 but the stationary collimator of FIG. 7 is replaced with a reciprocating collimator.

An optical structured (patterned) collimator (see FIGS. 3 and 4) such as a fiber optical bundle, mask or honeycomb-like device introduces its own transfer function into the transfer function of the imaging system (which includes the source and its collimator, the detector and its collimator, and the optical properties of the breast). Thus, the signal recorded by the detector(s) represents the superposition of all elements of the imaging chain. In addition, a fiber of the fiber bundle may be seen by more than one detector element. The adverse effects of an optical structured post-collimator pattern (such as a fiber bundle) on image quality can be reduced by moving the optical structured (patterned) collimator in a reciprocating fashion in front of the detector (See FIG. 8a, 11b).

Active collimation (in which the subject is modified rather than the optical beam in order to achieve scatter reduction) can be implemented by using compression plates to compress the region of the breast which is to be imaged. This reduces the effective volume of tissue a photon is likely to sample (and thus suffer additional scatter) before exiting the breast. The use of active collimation can be of particular value when time-resolved optical imaging techniques are employed. A variety of time-resolved optical imaging techniques (e.g. time-of-flight, holography, heterodyne, homodyne, Raman amplification, etc.) in development for use with highly scattering media exploit temporal or phase properties of the radiation field. See R. Berg, et al., SPIE Vol. 1511, p. 397–424, (1993). For example, if the light (radiation) source is pulsed and the pulse length is sufficiently short, time-of-flight (TOF) imaging and analysis (typically based on the "ballistic" and sometimes the "snake" component(s) of the radiation field) can be employed. Photon diffusive wave imaging (and spectroscopy) techniques (also referred to a frequency domain or photon migration or photon density wave techniques) may represent an alternative to time-resolved optical methods. Amplitude and phase modulation (and even phase encoding) have been utilized for composition and location identification. Photon diffusive wave computed tomography (CT) imaging has also been implemented. In addition, tomographic reconstruction techniques (several which make use of a reference medium) based on diffusion equation approximations to transport theory for thick tissue have been investigated. See, e.g., J. Fujimoto, 4 Optics & Photonics News 9–32 (1993); and Medical Optical Tomography, SPIE Vol. 1511, (1993).

In addition, it has been disclosed that the manner in which radiation interacts with a medium can be altered by the presence of an acoustic field. See, e.g., A. Korpel, *Acousto-Optics* (1988); and F. Marks, et al., "A Comprehensive Approach to Breast Cancer Detection Using Light," SPIE vol. 1888 pp. 500–510, (1993). Changes in the local optical properties of tissue can be measured by intersecting an acoustic field with a radiation field (see FIG. 4). Specific implementations can provide three dimensional information.

A problem addressed in co-pending application Ser. No. 08/480,760, by the present inventors, is that human skin has an index of refraction for non-ionizing radiation significantly different from that of air. In addition, human skin is not smooth on a microscopic scale and may also exhibit irregularities on a macroscopic scale. In cases where a transparent compression plate used to flatten the breast at the entrance and/or exit points of the optical radiation beam makes poor optical contact with the skin, or when a compression plate is not used at all (see FIG. 9) then the incident radiation and the exit radiation will be partially reflected and experience additional scattering at the skin surface. A coupling material (such as an appropriate gel or liquid) can be used to reduce the index of refraction mismatch between the skin and the adjacent medium (such as air or a compression plate). See co-pending application Ser. No. 08/480,760, by the present inventors.

In addition, breasts are non-homogenous objects which lack uniform physical dimensions. The thickness of breast tissue over a region to be imaged may not be consistent. If time-resolved optical imaging techniques are employed (e.g., used in heterodyne detection, TOF, holography, etc.), then the optical flight time between source and detector (typically a fixed distance apart) depends not only on the types of tissue encountered as radiation passes through the breast, but also on the total thickness of tissue the light must traverse. A compression plate (enabling shaping a region of the breast) and/or a coupling material can be used to reduce variations in path length.

A further improvement may be the use of optically absorptive materials on parts of the compression plate(s) in order to reduce the level of scatter which could ultimately reach the detector by re-entering the breast. Materials can also be selected on the basis of their acoustic properties if appropriate.

There may be disadvantages associated with imaging from a single direction, which has traditionally produced the familiar projection image common in x-ray radiography. Computed tomography (CT) enhances the available data set by acquiring projections from many directions, permitting three dimensional information to be synthesized from two dimensional data sets. By coupling a collimated beam into the breast (preferably with compression plates or modified compression plates) over a range of angles, angled transmission and backscattered images can be acquired. The data from these multiple projections can be combined to synthesize a three dimensional image (similar to "tomosynthesis" which is practiced in x-ray radiography). If the tissue volume of interest contains contrast-enhancing materials or materials which can be detected through emission fluorescence or Raman scattering (see, J. Wu, et al., Applied Optics Vol. 34, p. 3425–3430 (1995)) or Doppler effects, then the use of multiple collimated angled beams may improve localization capabilities. The angled transmission and backscatter measurements can also be made in conjunction with an intersecting acoustic field.

Angled incident beams or adjacent parallel beams have been used to provide a measurement for an estimated scatter correction in the collimated output. The radiation scattered in the appropriate direction can also be used as a virtual collimated beam. This virtual beam appears to originate from a tissue volume different from the externally incident collimated beam. Multiple projections can also be acquired using the virtual collimated beam data. Virtual collimated beam information can also be used to enhance the tomosynthesis image based on the collimated optical beam data.

The advantages of using compression plates were described earlier. In some instances it may be beneficial to modify the design by providing an open area in the compression plate where only air or a coupling fluid/gel are in contact with the skin surface of the area to be imaged. The region of the breast in the open area will still be of a relatively uniform thickness. Such an open area can be implemented for one or both plates. An open area compression plate can be used with the previously discussed optical and acousto-optical imaging techniques, and also to couple acoustic radiation into the compressed breast. The effect of this acoustic radiation beam (which can be tilted manually or electronically if desired) on tissue can be observed with an intersecting optical beam (which can also be tilted if desired). In addition, acoustic imaging techniques benefit from compression since tissue thickness over a region can be reduced significantly. The concepts of multiple transmitted and backscattered collimated angled optical beams, virtual collimated optical beams, and tomosynthesis can now be extended to include acoustic radiation beams.

Compression plates, with or without an open area, reduce the effective volume of tissue which needs to be evaluated and therefor can be useful for uncollimated sources and receivers as well as the collimated designs we have discussed. Thus, compression plates can be used to an advantage for conventional uncollimated diffuse and diffusive wave optical or acoustic (or acousto-optic) imaging techniques.

A new device and/or mode of imaging breasts using optical, acousto-optical, and acoustic non-ionizing radiation imaging techniques is needed to improve image quality and tissue characterization accuracy. Particular problems which need to be addressed are the thickness of a typical breast for optical, acousto- optical, and acoustic data acquisition, the need for improved radiation coupling into and out of the breast, the desirability of sampling volumes of uniform thickness, the need to enhance the information content of detected radiation, and the desirability of sampling a tissue volume from more than one direction.

Prior devices and methods do not address these concerns.

SUMMARY OF THE INVENTION

The present invention is a device and method which address the problems of the prior art. These problems are addressed through the use of compression devices, radiation coupling materials, various collimation techniques, various types of sources, and the use of multiple collimated angled beams (including normal incidence).

The present invention comprises an apparatus and method directed to enhancing the image obtained from a high resolution breast imaging device utilizing nonionizing radiation having a narrow spectral bandwidth. In addition, the present invention addresses the problems associated with acquiring image data from a single perspective (such as normal incidence) or at a constant initial depth (the surface of the skin). Modified compression plates and optical (radiation) coupling materials (e.g., a fluid such as water or a gel) can be used to ensure efficient coupling of a collimated beam into and out of the breast. An acoustical system can be combined with compression plates and/or optical scanning to provide additional tissue information.

The present invention utilizes a collimated light (radiation) source of narrow spectral bandwidth (such as generated by a laser, waveguide, phased array, etc.) to produce a beam or a number of beams of relatively small spatial dimensions which, in turn, are used to obtain images of a breast with high spatial resolution. The radiation source requirements may range from a continuous (CW) to a rapidly pulsed source. If the source produces a beam with a sufficiently short pulse (or coherence length), then the beam can be relatively small in three spatial dimensions instead of two spatial dimensions (typically regarded as the beam cross-section normal to the beam axis). The rate at which a source is pulsed should preferably be rapid enough to ensure that an adequate integrated signal is detected before patient motion becomes a problem. However, the energy per pulse should preferably not be so high as to violate radiation safety guidelines. Additional features of a source might include being frequency-tuneable, being polarized, having a CW-modulated, coded or complex waveform, etc.

The breast to be imaged is preferably compressed. However, the compression plates used to compress the breast need not be of the same size and one or both plates can be fixed or mobile. Greater compression (reduction in optical path length) is possible if a small area of the breast is compressed rather than compressing the entire breast at once (which is typical for traditional x-ray mammography). It is possible to contour one or both plates in order to obtain additional compression beyond that expected from a reduction in plate size alone while reducing patient discomfort associated with breast compression. The compression plate or plates can be modified to include an open region which would provide improved access to the surface of the breast. The use of a compression plate(s) can be considered to be a form of active collimation in which the subject is modified in order to improve the quality or information content of the detected radiation beam. As is described above, a reduction in optical (radiation) path length by reducing the effective scatter volume aids in scatter reduction, improves image sensitivity, and reduces the power requirements of the optical source. Therefore breast compression is preferable when a collimated optical source is employed. Compression is particularly useful if time-resolved optical methods (e.g., TOF, including the use of ballistic and/or snake-like components, holography, Raman-amplification, heterodyning, homodyning, etc.) are implemented since the thickness of a typical breast may otherwise represent a severe drawback. Diffusive wave imaging techniques will also benefit from a reduction in path length.

The present invention can also utilize an optical coupling material, such as a liquid or gel, to improve radiation coupling between air or compression plate and the skin surface of the subject breast. The coupling material can also aid in the dissipation of heat from the region being irradiated and function as a lubricant for components that might slide over the breast. An optical coupling material (with appropriate index of refraction and/or scattering properties) can also be used to minimize discrepancies in the path length differences due to non-uniform tissue thickness over a region of interest. This is particularly important for techniques which utilize phase or temporal properties of the radiation field, such as pulsed radiation which is evaluated by utilizing TOF analysis. The detector unit in a TOF acquisition system has the capability of ignoring all but a segment of the exiting radiation pulse (typically by employing a chopper such as a Kerr cell or electronically through the use of a gated detector such as an intensified camera, a photomultiplier tube or a streak camera). Optical coupling materials can be chosen on the basis of their absorptive properties as well as their index of refraction and scattering characteristics, thereby potentially providing preferential scatter reduction of radiation which travels a longer total path through the absorptive optical coupling material.

The present invention relates to imaging breasts using optical, acousto-optical, and acoustic non-ionizing radiation imaging techniques which will improve image quality and tissue characterization accuracy. The present invention also relates to imaging breasts using multiple collimated angled beams (including normal incidence). Virtual collimated radiation beams can be generated from the multiple collimated angled beams and also used for imaging and/or image enhancement. Since the source requirements can range from CW to pulsed, conventional optical collimation techniques as well as time-resolved, diffusive wave, etc., optical methods can be used to evaluate the angled collimated beams and the virtual collimated beams. Multiple two dimensional images can be acquired for transmission and backscatter angled and virtual collimated beams. Three dimensional image information can be synthesized from the multiple angled collimated beams data, the multiple virtual collimated beams data, or an appropriate combination of the two sets of data. The use of multiple angled and virtual collimated beams can enhance the capability of an imaging system to localize the presence of materials which can be recognized from emission fluorescence, Raman scattering, or Doppler effects. Collimation requirements can vary from highly collimated to weakly collimated depending on the application. For example, a weakly collimated detector might comprise a conventional detector coupled to a surface of a breast by a large core optical fiber, permitting acceptance of photons with a wide range of direction vectors while still limiting the optical field of view or area of the breast surface which is observed. Such weak collimation is useful, for example, for measuring diffuse radiation.

The present invention also relates to acquiring additional information about tissue characteristics by intersecting an acoustic radiation field with an optical radiation field used to image the tissue.

The present invention also relates to improvements to compression plate design such that one or both plates have an open region adjacent to the skin surface. This open region typically allows air and/or a coupling fluid/gel to be in contact with the skin surface. Radiation from an acoustic source can also be coupled into and out of the open region (s), enabling compression transmission and backscatter (reflection) acoustic image data and acousto-optic image data to be acquired as well as optical image data. A conventional acoustic transducer(s) can be used to readout the exiting acoustic field. Ideally, the coupling fluid/gel would be appropriate for acoustical and optical coupling. In addition, optically absorptive coatings can be used to cover parts of a plates and so prevent unwanted scatter from reaching the detector. Acoustically absorptive coatings can be utilized when appropriate. A deformable mirrored deflection plate (similar to that employed in a scanning laser acoustic microscopy i.e., or SLAM) or reflective surface or elastic layer can be used to readout the acoustic waveform at the exit surface (which may also be the entrance surface). Such a deflection plate or surface could be integrated into a compression plate. One possible design is to use a deformable mirror coating which is reflective at the readout beam wavelength but transmissive at wavelengths used for optical imaging. The deflection plate or surface itself could function as an acoustic source or detector if it was made from a piezoelectric material such as a piezoceramic, a piezocomposite, or a piezopolymer such as polyvinylidene difluoride or PVDF. See SPIE vol. 1733 (F. Lizzi, ed., 1992); and G. Kino, Acoustic Waves: Devices, Imaging, and Analog Signal Processing (1987).

The combination of an open compression plate (recall that the compression plates need not be the same size) with an elastic or flexible layer of material across the opening can be thought of as a compression imaging bladder for optical, acousto-optical, and acoustic imaging. The rigid walls of the plate enable compression over a specific region while the layer provides a uniform interface and good contact with the skin surface or an intermediate coupling fluid. Such a compression imaging bladder provides the same benefit that an open compression plate offers of immobilizing a region of the breast and thus limiting the effect of patient motion. The compression imaging bladder also promotes a uniform thickness of coupling fluid/gel with tissue (ensuring that gaps or discontinuous regions of the breast surface are filled) over the imaging region while minimizing motion of the fluid/gel. A simple variation of this design allows a flexible bladder unit (which can be referred to as a an imaging bladder) to be inserted into the opening of the compression plate(s) rather than using a thin layer fixed to the compression plate(s). A source, a receiver, or both can be incorporated into this imaging bladder unit just as they could be incorporated into the compression imaging bladder. If the imaging bladder can be sealed and pressurized (providing relatively rigid walls), then compression can also be obtained by using only the imaging bladder without the compression plates. The compressive force is now applied to the frame of the imaging bladder rather than the compression plates (see FIG. 20). The compressive force can be used to push the bladder forward which will compress the breast or hold the bladder in place while the sealed unit is pressurized thereby compressing the breast. Thus the imaging bladder is modified into a variation of the compression imaging bladder. We shall refer to both compression imaging bladder and imaging bladders as bladders.

The present invention also relates to imaging using compression plates, with or without an open area, in conjunction with weakly collimated sources and receivers. Thus, compression can be used for conventional diffuse and diffusive wave optical or acoustic (or acousto-optic) imaging techniques.

DESCRIPTION OF THE DRAWINGS

FIG. 8b is a partial side view of the embodiment from FIG. 8a.

FIG. 11a shows a perspective front view of a use of a reciprocating patterned (structured) collimator.

FIG. 20 shows an open contoured compression plate and an imaging bladder. The bladder is shown as having an elastic layer attached to an external frame which can be used to provide a compressional force if needed or simply to ensure that the bladder and underlying breast surface are coupled efficiently. The elastic layer can be acoustically and/or optically transmissive. An acoustic source/receiver is shown as contained within the bladder/frame assembly. If it is sufficiently sealed, the bladder can be pressurized thereby providing sufficiently rigid expanding walls to compress a region of the underlying breast.

DETAILED DESCRIPTION OF THE PREFERRED EMBODIMENTS

Figure 1A:
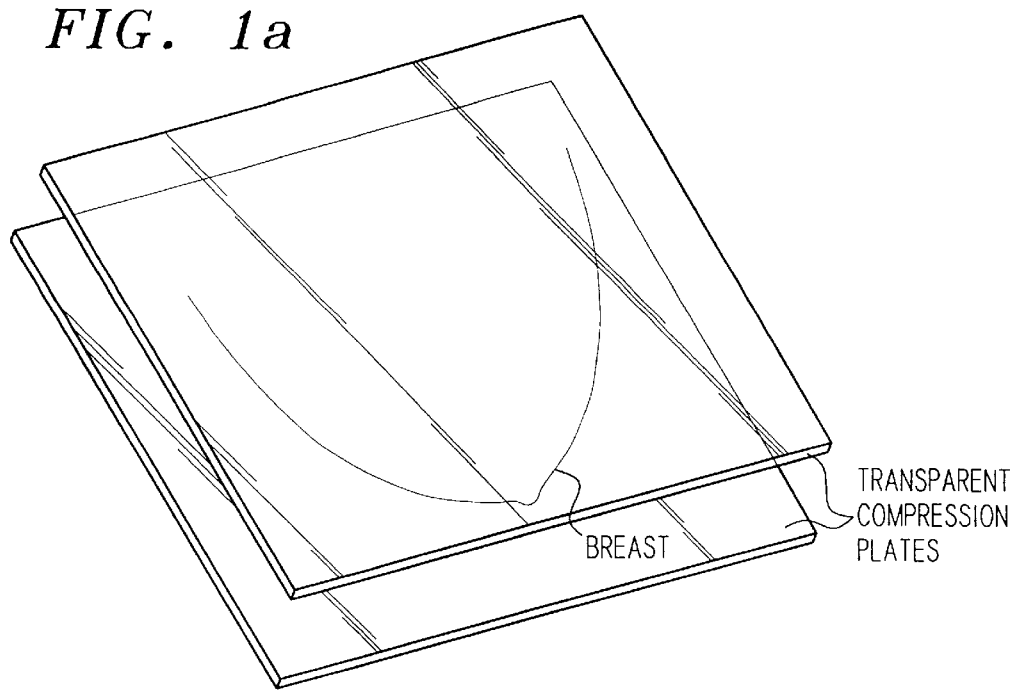
FIG. 1a is a perspective view of a breast being compressed between two compression plates. The compression plates are preferably transparent to the light (radiation) wavelengths to be used to image the breast. For illustrative purposes, the size of the plates is preferably similar to those used in conventional x-ray mammography. However, plate size can be reduced to permit imaging of small sections of a breast.
Figure 1B:
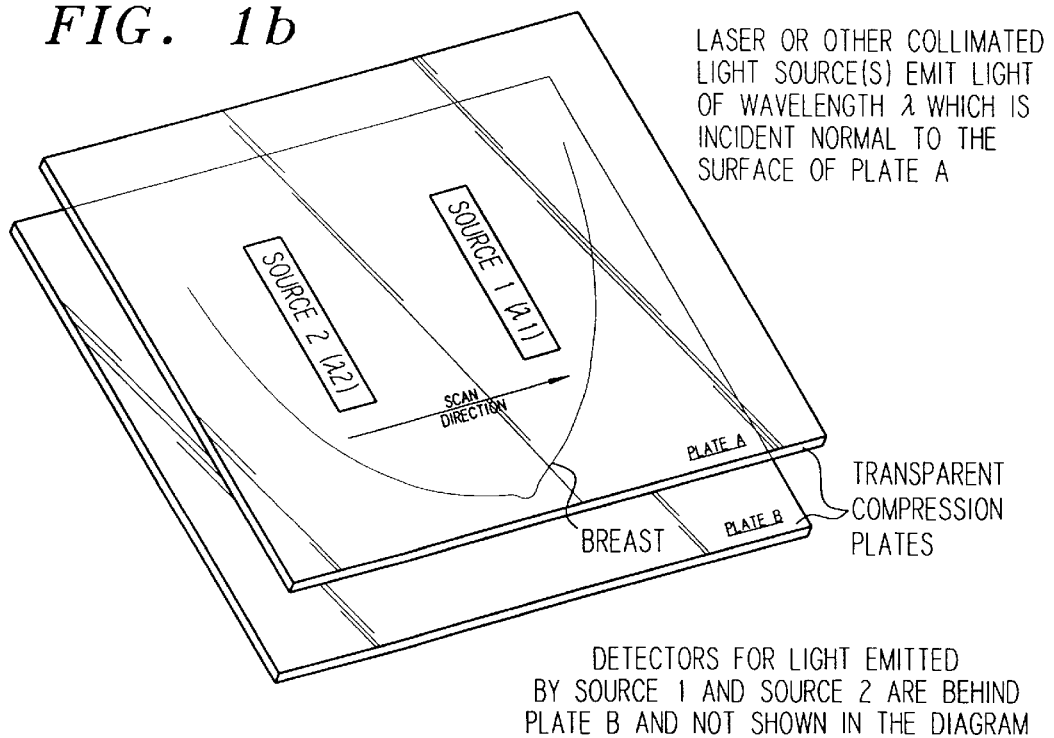
FIG. 1b shows a perspective view of FIG. 1a wherein one, two or more point, line, or two-dimensional sources, each source emitting collimated light (radiation) of a distinct wavelength, is/are moved parallel to the surface of a compression plate. A detector corresponding to each source moves in synchrony with its corresponding source parallel to the surface of a second plate. Analog signals from the detector(s) can be digitized and stored in computer memory for display, processing and/or analysis purposes.
Figure 2A:
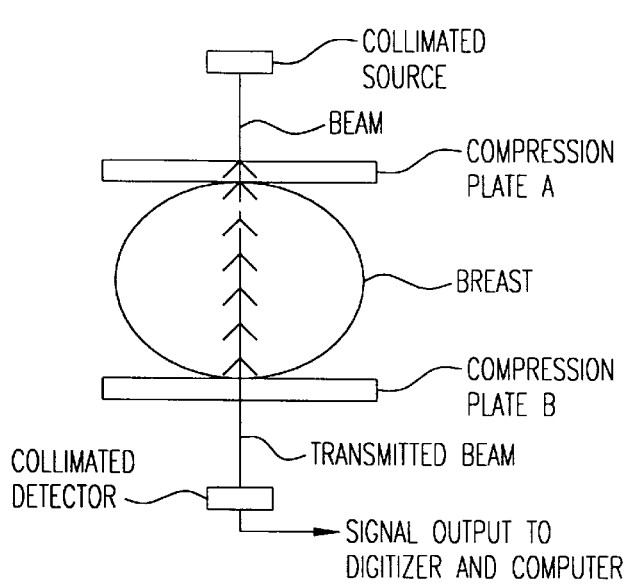
FIG. 2a shows a cross-sectional front view of a collimated pencil beam used in a raster scan format from a point source, through a breast compressed by two compression plates, and to a detector. The detector may also use post-collimation to help minimize detection of scattered light (radiation). Collimation techniques for scatter reduction can include air gaps, fiber optics, light pipes, masks, polarized filters, narrow spectral bandwidth filters, directionally sensitive filters, holographic or diffractive filters which exhibit high angular sensitivity, focused lenses, waveguides, focused arrays, or mechanical apertures.
Figure 2B:
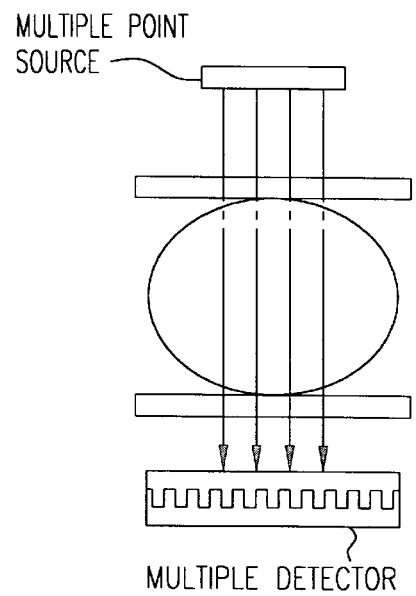
FIG. 2b shows a cross-sectional front view of multiple point beams used in a raster scan format to reduce image acquisition time.
Figure 2C:
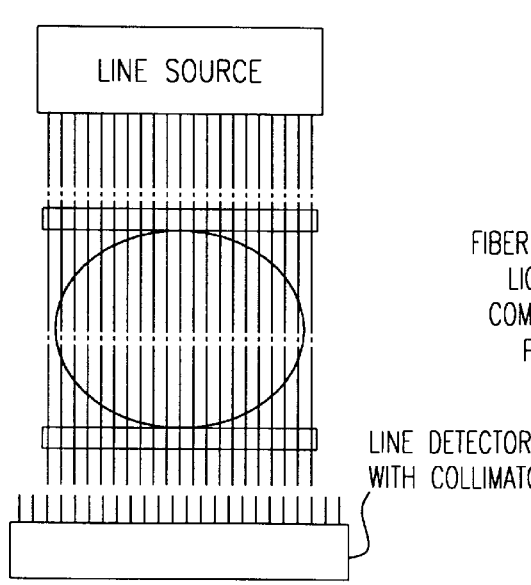
FIG. 2c shows a cross-sectional front view of a collimated (single or multiple) line beam of light providing a line scanning format. The array of detectors preferably use post-collimation to reduce detected light scatter from the subject.
Figure 2D:
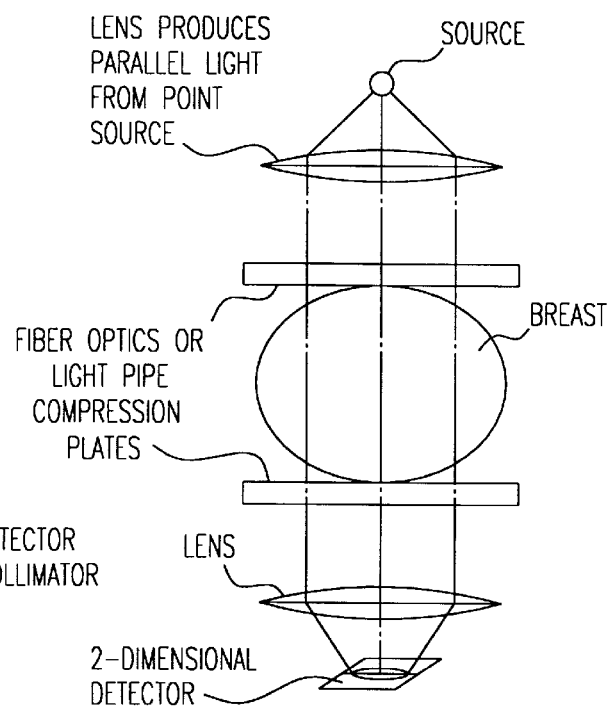
FIG. 2d shows a cross-sectional front view of a parallel light beam used for rapid image acquisition by a two-dimensional detector. In this case, post-collimation is incorporated into the compression plates.

The present invention is directed to enhancing the image obtained from a high resolution breast imaging device utilizing non-ionizing radiation, preferably having a narrow spectral bandwidth.

The present invention utilizes a collimated light (radiation) source of narrow spectral bandwidth (such as generated by a laser) to produce a beam or a number of beams of relatively small spatial dimensions which, in turn, are used to obtain images of a breast with high spatial-contrast resolution. Source requirements can range from CW to rapidly pulsed and thus may include modulated (AM and FM are common examples), coded, and complex waveforms. The beam size can be reduced by limiting the cross-sectional area of the beam (a conventional method of optical collimation) and by limiting the temporal width of the beam (i.e. using a short pulse width or a short coherence length) and, thus, limiting its spatial extent along the direction of propagation. The effect of reducing the cross-section of the optical beam is equivalent to adding a spatial filter since it helps to limit scatter cross-talk within the beam itself. Thus, a smaller "effective" volume of tissue is sampled from the perspective of the optical detection system.

Similarly, a reduction in breast thickness via compression reduces the optical path length and represents another type of optical collimation (i.e. a smaller "ineffective" volume of tissue can be sampled). Compression can be described as active collimation in which the radiation beam parameters are affected or controlled by modifying the subject (in this case the tissue volume of interest) whereas in the case of passive collimation radiation beam parameters are modified or enhanced directly. The use of compression enables the image acquisition requirements to be relaxed. For example, a larger scan beam area or closer proximity of beams (if multiple scan beams are employed simultaneously) may be permissible during image acquisition. Because optical scattering in tissue is so severe, the relative benefit of employing compression for optical breast imaging is much greater than for x-ray mammography. Reducing the optical path length aids in scatter reduction, improves image sensitivity, reduces patient exposure, reduces the possible tissue volume being interrogated (increasing our a priori information about what is being analyzed), and reduces power requirements of the optical source. Therefore, breast compression is preferable when conventional optical collimation is employed. Compression is particularly useful if time-resolved optical methods (e.g., TOF including use of ballistic and/or snake-like components, holography, Raman-amplification, heterodyning, homodyning, etc.) all implemented since the thickness of a typical breast would otherwise represent a drawback. Diffusive wave imaging techniques as well as fluorescence lifetime and even simple diffusive imaging techniques would also benefit from a reduction in the volume of tissue responsible for modifying the wave. The use of compression also permits the creation of a region of uniform thickness (desirable for time-resolved optical methods) and the ability to shape (typically flatten) the optical beam entrance and exit surfaces. Therefore, it is preferred that the breast to be imaged be compressed during imaging.

Figure 8A:
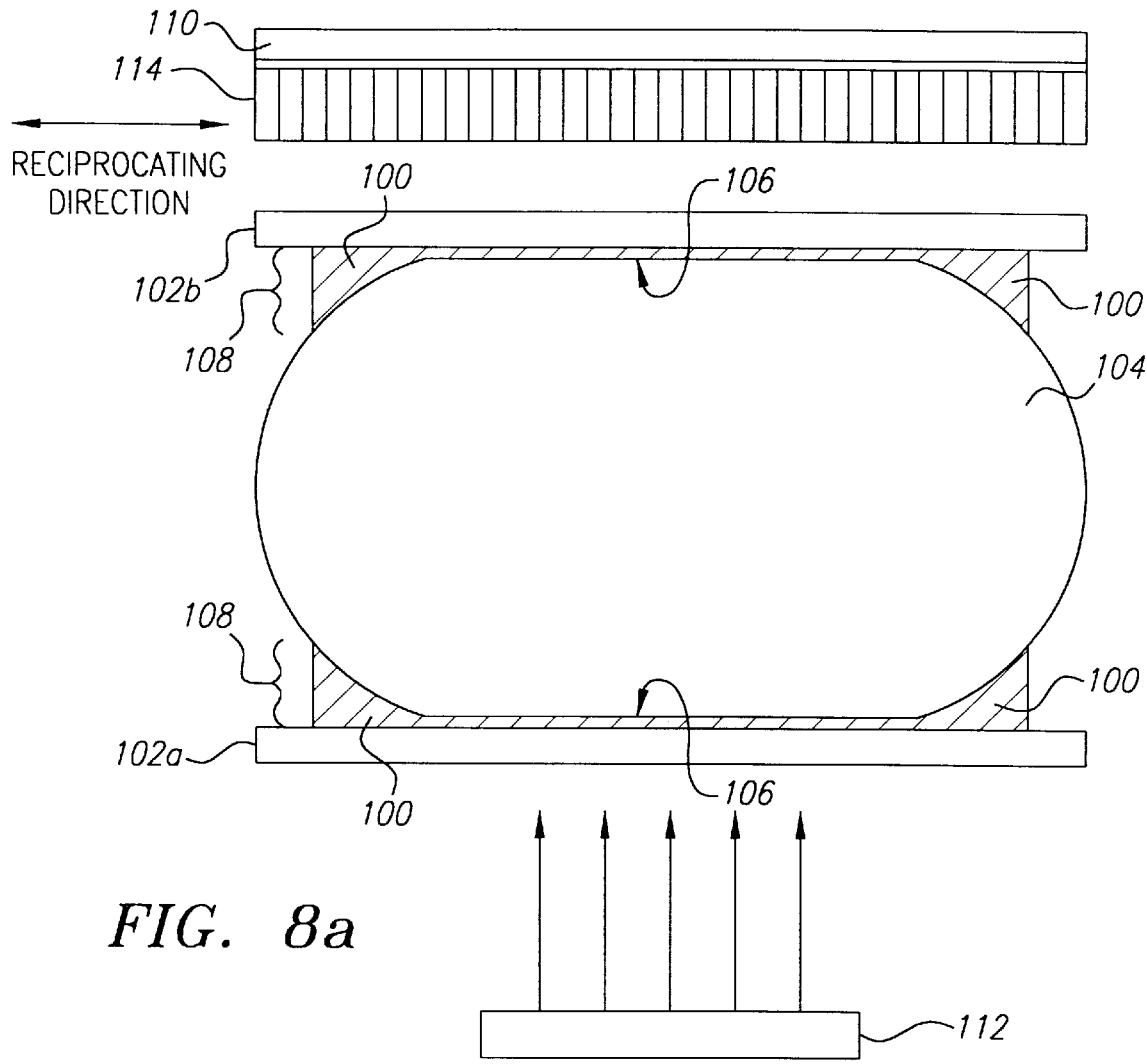
FIG. 8a shows a front view of one embodiment of the present invention wherein optical coupling material is used in breast imaging and reciprocating patterned collimators are used in optical breast imaging.
Figure 8B:
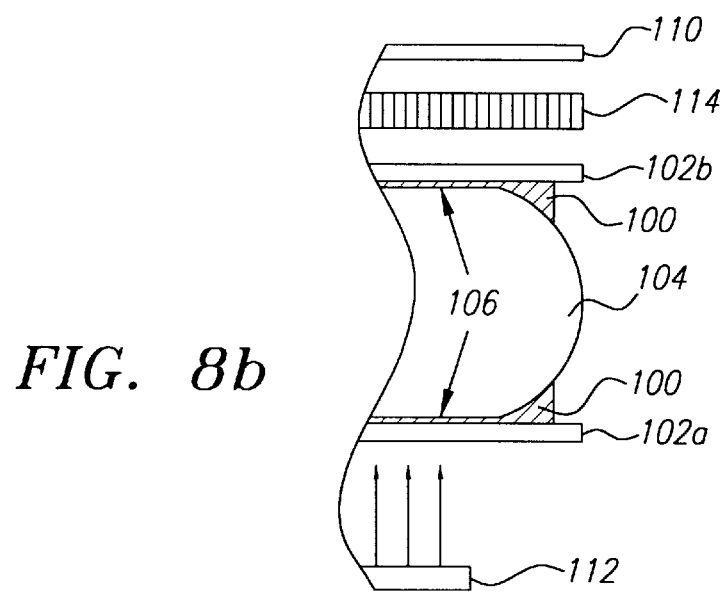
Figure 9A:
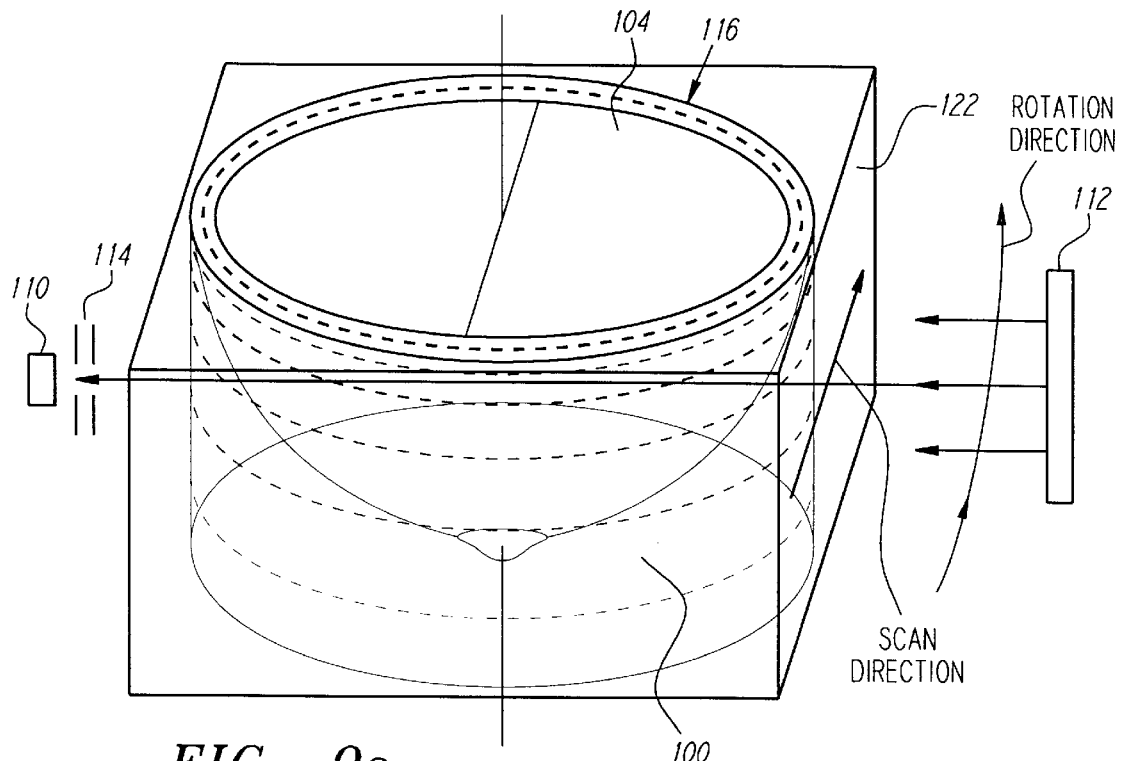
FIG. 9a shows a partial side view of an embodiment of the use of optical coupling material and collimators in optical computed tomography.
Figure 9B:
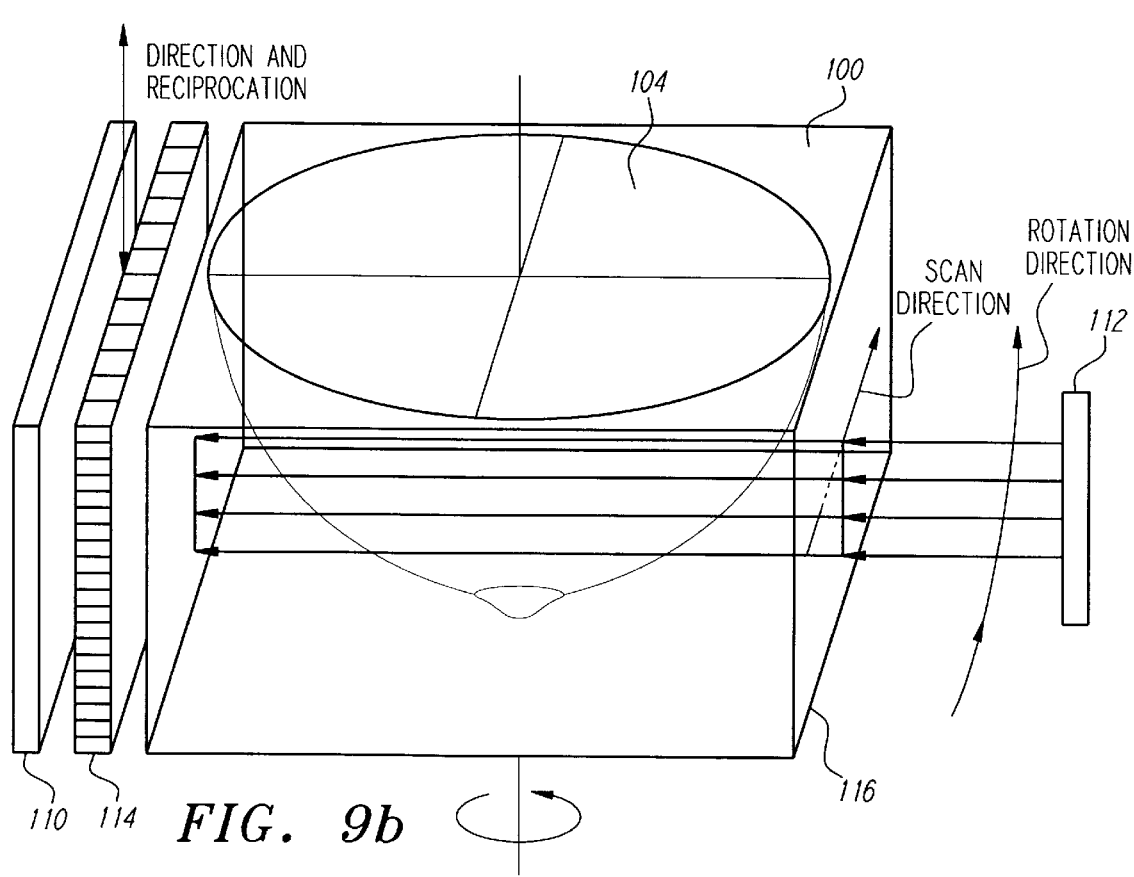
FIG. 9b shows a partial side view of a second embodiment of the use of optical coupling material and reciprocating patterned collimators in optical computed tomography.
Figure 12:
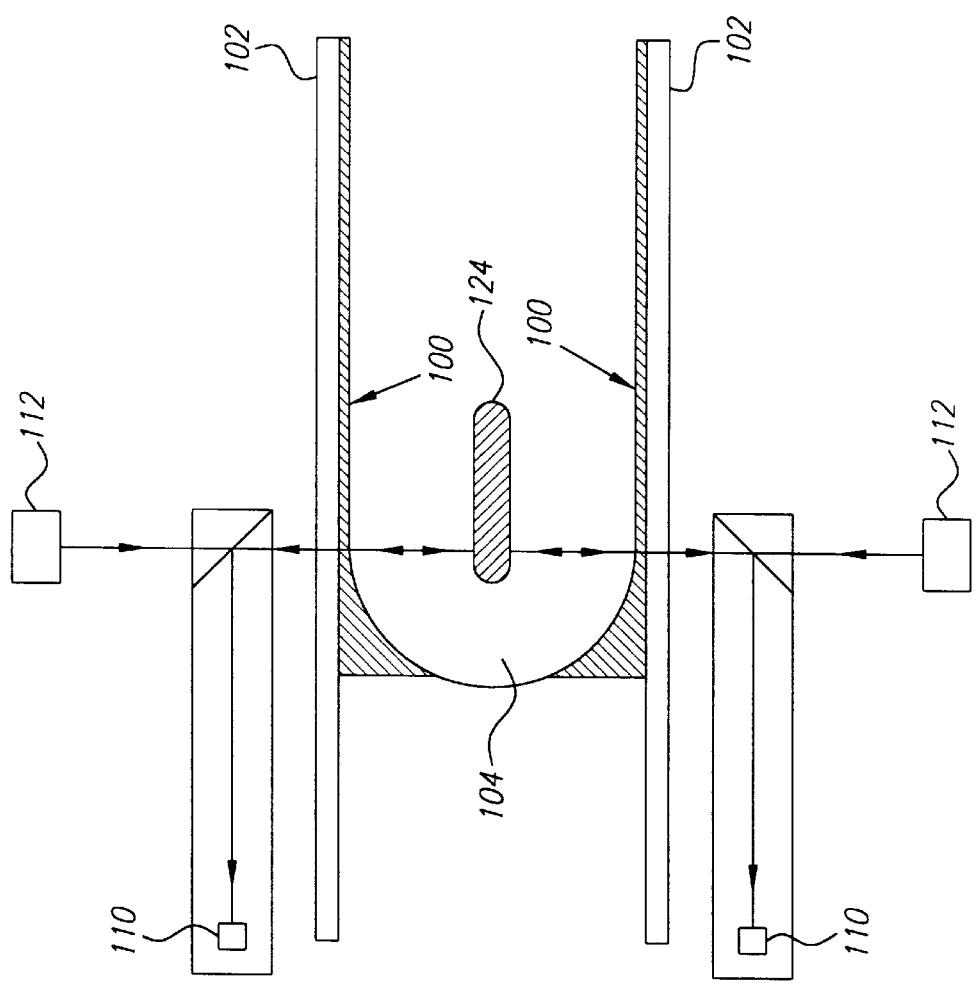
FIG. 12 shows a cross-sectional side view of two units being used to collect backscattered radiation on opposite sides of a breast, such that each unit collects backscattered radiation and transmitted radiation, permitting two sets of measurements to be made.
Figure 13A:
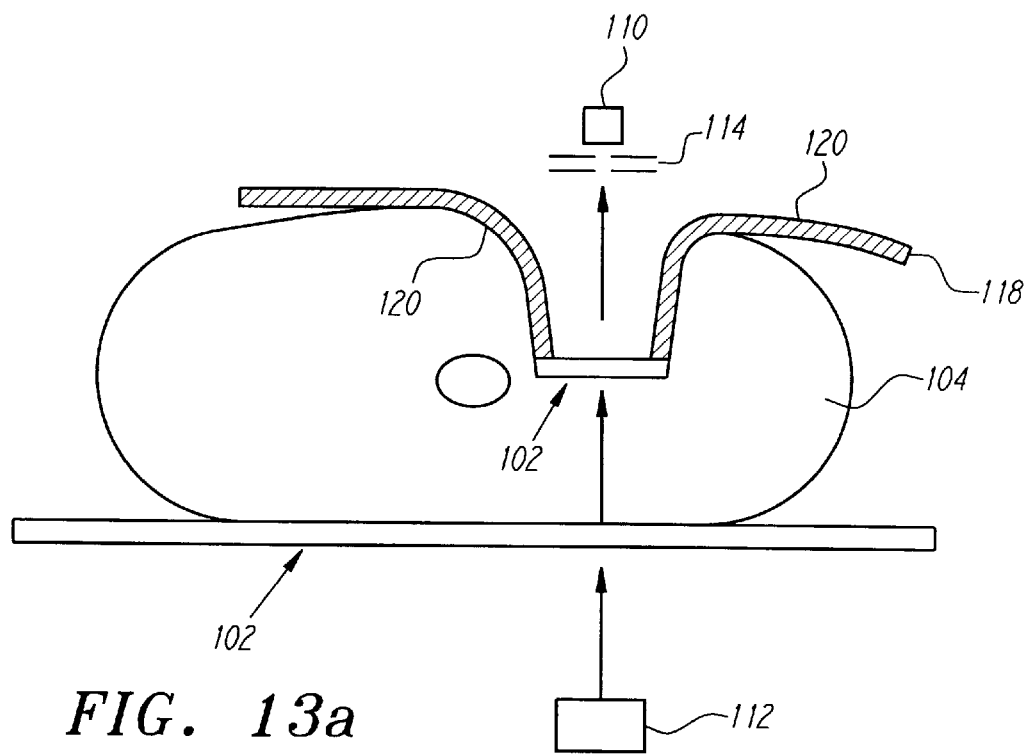
FIG. 13a shows a front view of an embodiment of a contoured compression plate.
Figure 13B:
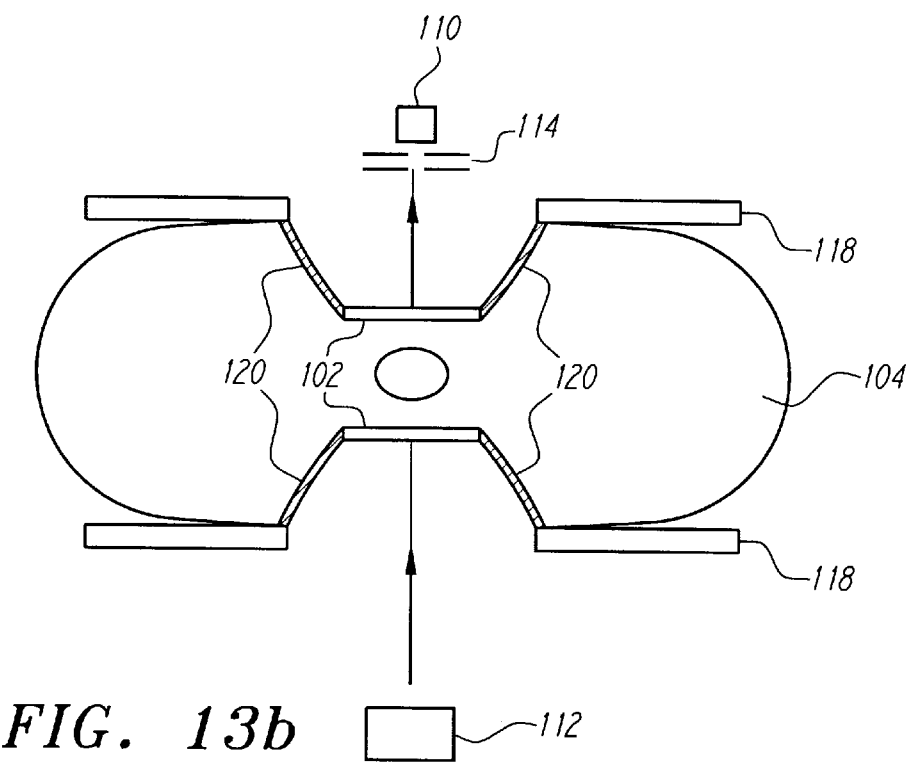
FIG. 13b shows a front view of a second embodiment of a pair of contoured compression plates.

The compression plates used to compress the breast need not be of the same size and one or both plates can be fixed or mobile. Greater compression (resulting in a greater reduction in optical path length) is possible if a small area of the breast is compressed rather than compressing the entire breast at once. Compare, for example, FIG. 8a with FIG. 13a. It is typical in traditional x-ray mammography to compress the entire breast at once. As shown by comparing FIG. 8a to FIG. 13a, a reduction in the size of plates 102 permits imaging small sections of the breast 104 and, thus, decreases problems due to gaps 108. In one embodiment two small, aligned plates are moved over the breast surface, acquiring many small images. In another embodiment, small regions are scanned by positioning a large fixed plate on one side of the breast while a smaller plate is moved over the opposite side. In alternative embodiments one or both plates are contoured to attain additional compression (and, therefore, a reduction in optical path length) beyond that expected from a reduction in plate size alone. As is shown, for example, in FIGS. 13a and 13b, contouring one (FIG. 13a) or both (FIG. 13b) plates 118 allows compression beyond that expected from a mere reduction in plate size and, therefore, further reduces the optical path length and improves the imaging. As is shown in FIGS. 13a and 13b, the contoured plates 118 preferably comprise a transparent portion 102 and an opaque portion 120. Contouring one or both plates has the added advantage of lowering the level of patient discomfort typically associated with breast compression. The type of contour to be used depends upon the scanning technique (such as a continuous scan or a scan where compression is removed and then reapplied before the next region of the breast 104 is scanned) and the amount of compression desired.

Figure 3:
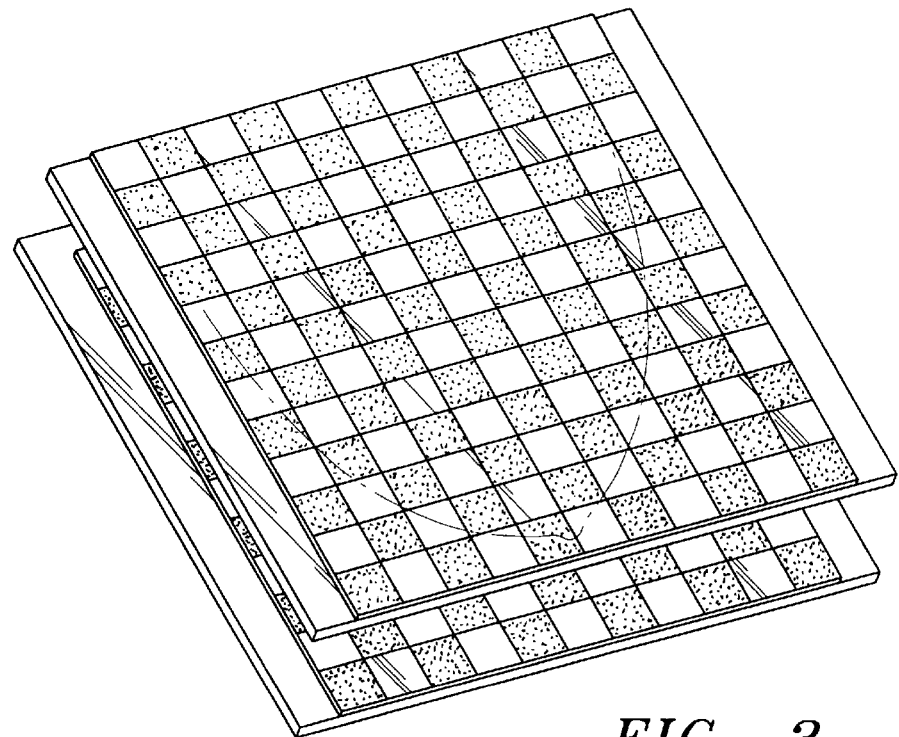
FIG. 3 shows a perspective view of a breast being compressed between two compression plates (as in FIG. 1) wherein additional plates comprise a patterned mask of the checkerboard-type for use as a collimator.
Figure 4:
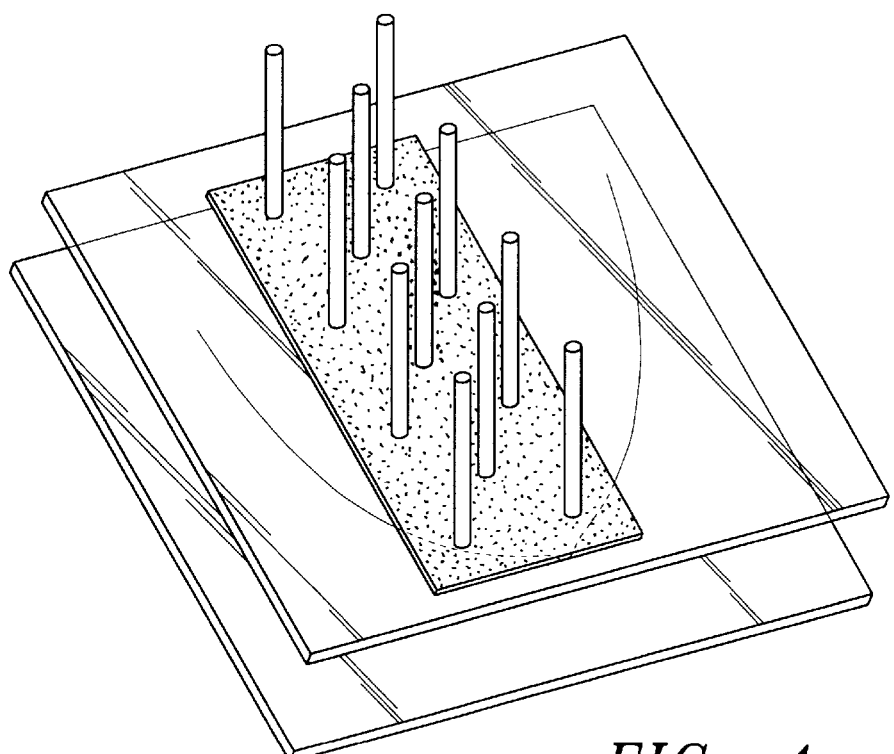
FIG. 4 shows a perspective view of a breast being compressed between two compression plates (as in FIG. 1a) and construction of a virtual mask comprised of a matrix of fiber optic pipes which are spaced apart.
Figure 5:
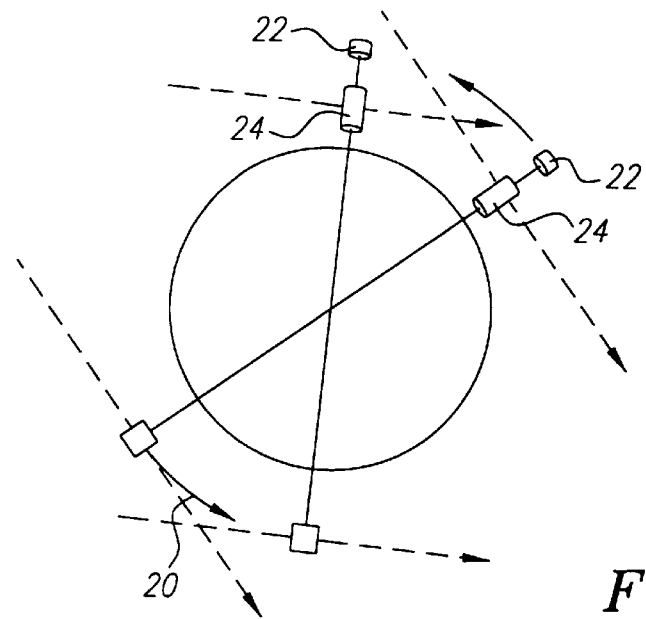
FIG. 5 shows an on-axis view of the use of collimators in an optical computed tomography arrangement.
Figure 6:
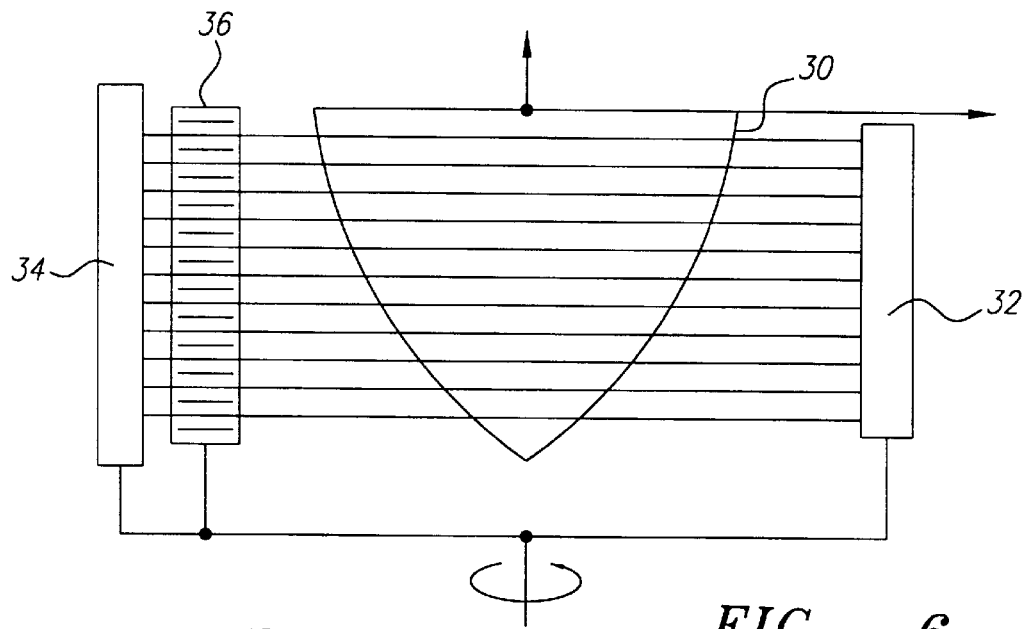
FIG. 6 shows a cross-sectional view of the use of a collimator in optical computed tomography.
Figure 7:
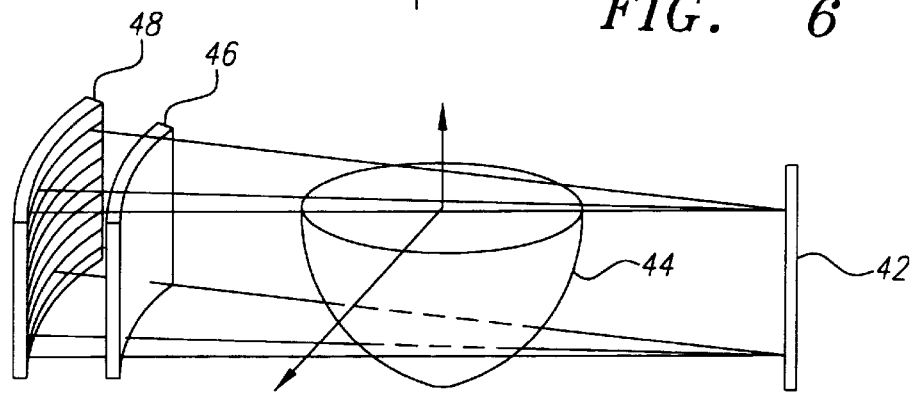
FIG. 7 shows a perspective view of a multiple fan beam scanning arrangement in optical computed tomography.
Figure 15:
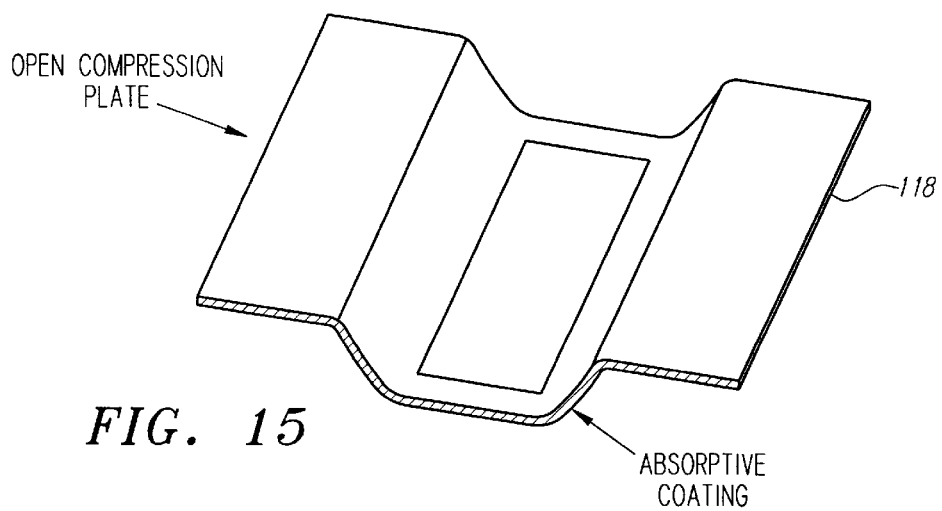
FIG. 15 shows an open contoured compression plate with absorptive coating(s) applied to certain surfaces.

As shown in FIG. 15, the compression plates need not be solid pieces, openings can be incorporated into the plate(s) such that the entrance or exit radiation beams avoid transmission through the plate(s). In addition, compression plates need not be totally transparent. Areas that are not used to transmit radiation can be coated with radiation-absorptive materials (which may be appropriate for optical or acoustic radiation) to reduce the transmission and/or reflection of unwanted radiation. The use of masks as shown, e.g., in FIG. 3, or of collimators built directly into the compression plates as shown in FIG. 2, can be used to limit the effects of undesirable exiting radiation.

If the entering or exiting radiation must pass through a compression plate, then it is preferable that the appropriate region of the compression plate is made of a suitable material with an index of refraction which closely matches the index of refraction of the materials adjacent to interior surfaces of the plate which may be the skin of the breast or, preferably, an optical coupling fluid (e.g., water) or gel.

Imaging a breast via the various methods described herein can be improved by the use of optical (i.e., radiation) coupling materials such as index matching liquids (e.g., for example, water) or gels in contact with the radiation entrance and/or exit surface(s) of the breast. The optical coupling material properties (e.g., index of refraction and scattering and absorption properties) can be selected for a particular imaging format, tissue type, and optical spectrum. The optical coupling material can also help dissipate local buildup of heat for the region being irradiated as well as provide a lubricant, particularly for moving components in contact with it.

Since many versions of this invention are possible, light (radiation) sources may range from continuous (for example CW or modulated CW) to rapidly pulsed. Controlling the optical (radiation) pulse width, the degree of optical collimation (including the size or area of the input beam), the frequency or phase, the amplitude, the spectral composition, the coherence, and the degree of polarization of the radiation are methods of encoding or controlling the properties of the optical source. A number of collimation methods (e.g. by air gaps, fiber optics, light pipes, masks, polarized filters, narrow spectral bandwidth filters, directionally-sensitive filters, narrow spectral bandwidth and directionally-sensitive filters, focused lenses, waveguides, focused arrays, holographic or diffractive spatial filters as well as acousto-optic devices which exhibit high angular sensitivity, a reciprocating collimator, or mechanical apertures) are available for enhancing image quality.

The waveform emitted from the optical (radiation) source can also be controlled. A number of phase, frequency, and noise-resistant coded waveforms (for example, chirp pulses) have been used in radar, (see, e.g., D. Wehner, High Resolution Radar, Chapters 3 and 4, (1987); and M. Soumekh, Fourier Array Imaging (1994)) in acoustics (ultrasound, underwater, geophysical), in optical communications (e.g., a "complex" waveform such as a soliton pulse), in electronic communications (see, e.g., H. Rowe, Signals and Noise in Communication Systems, (1965); and C. Nagasawa, et al., Applied Optics, vol. 29, no. 10, p. 1466–1470 (1990)), and in encryption, and can be applied to optical imaging of stationary or moving tissue. Such waveforms permit decoding (essentially, matched filter processing) of the transmitted or backscattered signal and, thus, allow a comparison of how beam properties such as coherence, amplitude, spatial distribution, phase, spectrum, and relationship between pulses (for example, pulse patterns or sequences) or wavefronts, etc., are modified by the tissue through which the beam passes.

For example, a light source can be frequency or amplitude modulated using a specific waveform or pattern. Thus, sinusoidal wave amplitude modulation could be employed to measure information about wave-front propagation. The effect of breast tissue on a complex waveform can also be evaluated. For example, by using a source of soliton pulses and an appropriate collimated receiver which may include a fiber amplifier. See, e.g., H. Haus, Molding Light Into Solitons, IEEE Spectrum, 48–53 (March 1993). Temporal or phase properties of a pulse or wavefront can be utilized to provide additional beam collimation. A number of time-resolved optical imaging techniques have been developed for use with highly scattering media, ultrafast phenomena, etc. These applications exploit temporal or phase properties of the radiation field (e.g. time-of-flight, holography, heterodyne, homodyne, Raman amplification, etc.). For example, if the light (i.e., radiation) source is pulsed and the pulse length is sufficiently short, conventional TOF imaging and analysis (typically based on the "ballistic" and sometimes the "snake" component of the radiation field) can be employed. The ballistic, snake, and diffuse components of the signal (the temporal profile) can each be acquired and evaluated independently as well as together. Source-detector imaging formats which implement a time-resolved technique tend to work well for thicknesses of breast tissue that are relatively thin compared to the actual thickness of a typical breast. Further improvements in mammography image quality, when time-resolved optical techniques are employed, typically require the use of conventional collimation for additional scatter reduction. See, A. Sappey, Applied Optics, Vol. 33, No. 36, p. 8346–8354, (1994). A uniform thickness of tissue and especially the ability to compress the breast or a region of the breast would prove beneficial if a time-resolved optical technique is utilized. Advanced statistical techniques can be applied to the additional information gained concerning how normal and diseased tissue affects the temporal profile, phase, amplitude, spatial, polarization, and spectral content of the radiation waveform or pattern. This will enhance the process of image reconstruction. See Image Recovery Theory and Application (H. Stark ed. 1987).

Figure 10:
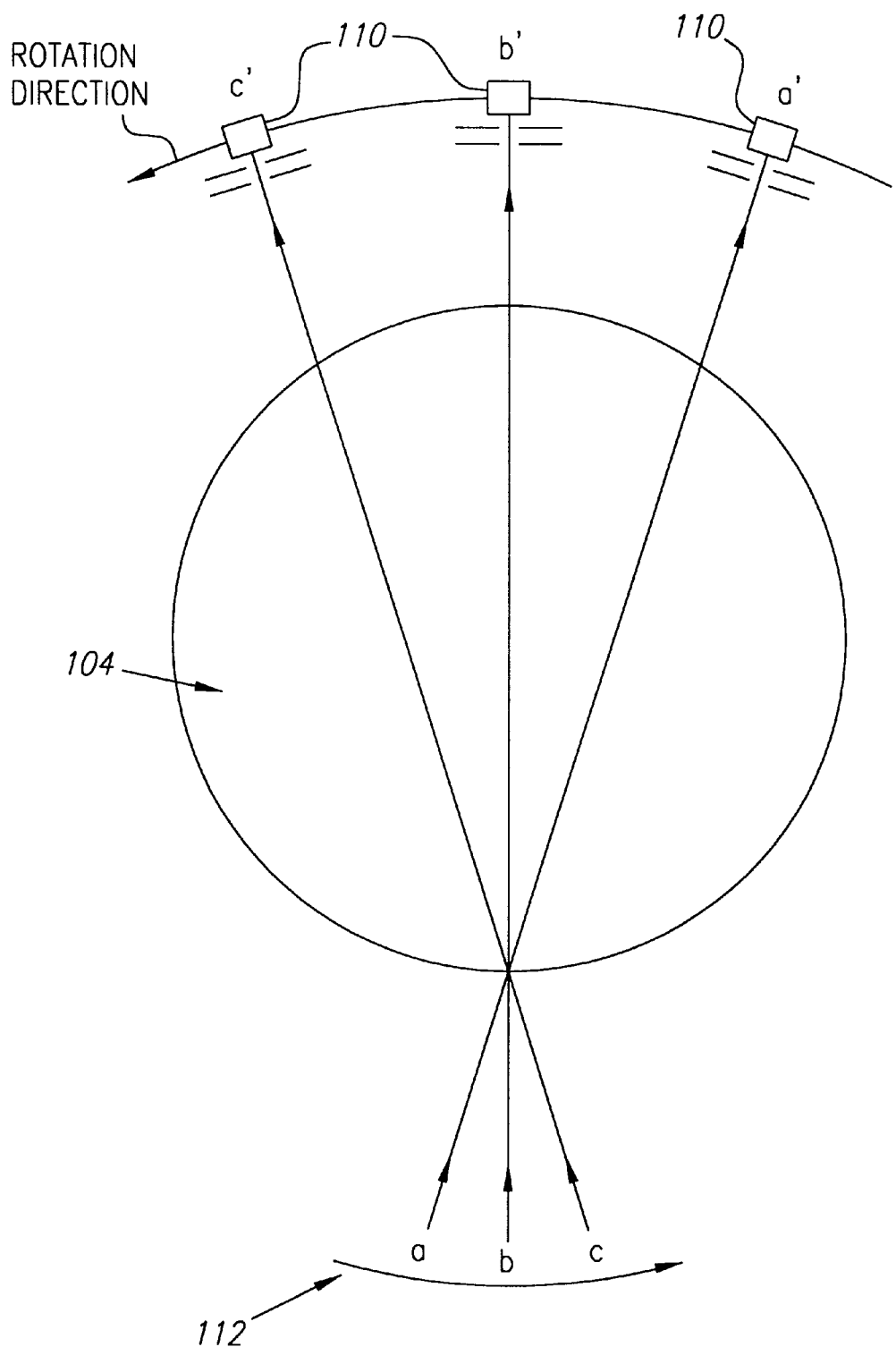
FIG. 10 shows an on-axis cross-sectional view of a third embodiment of optical computed tomography.
Figure 11B:
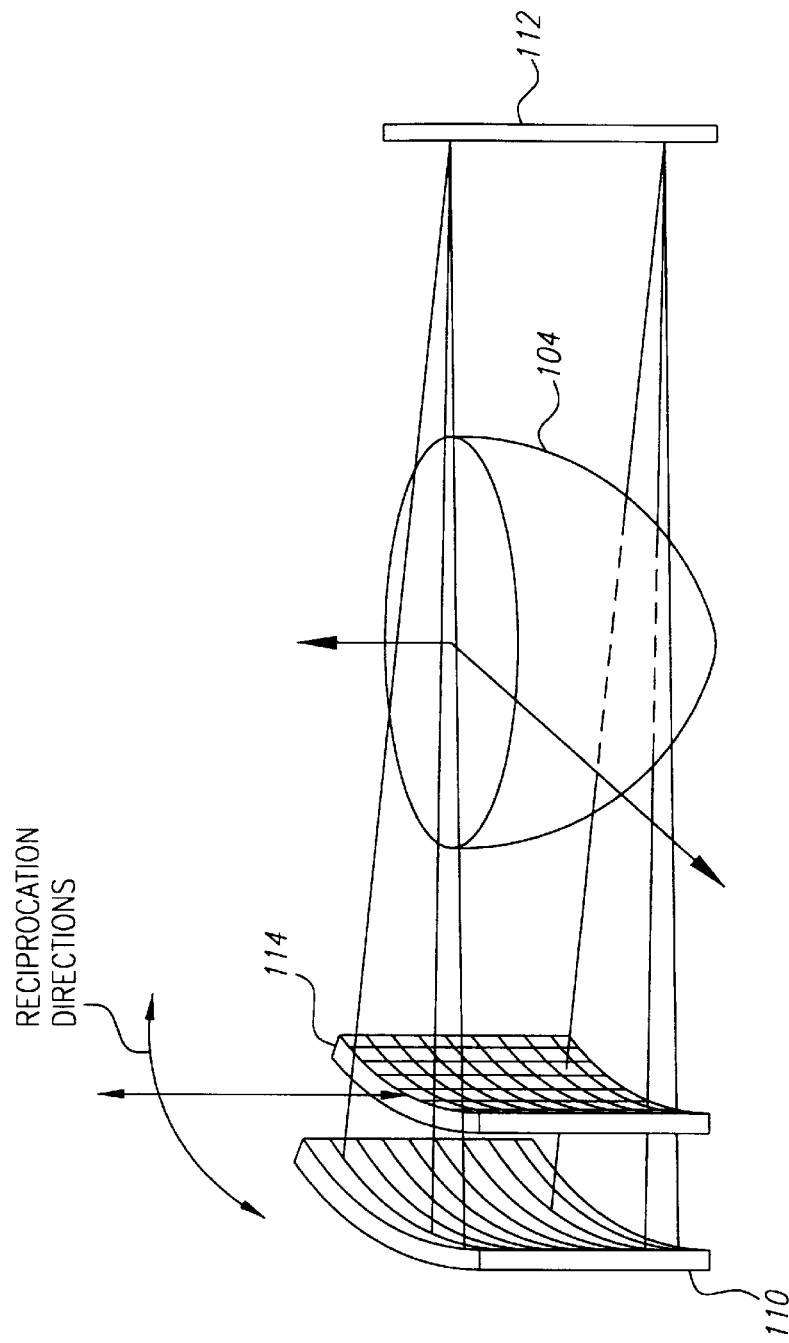
FIG. 11b shows perspective side view of a multiple fan beam scanning arrangement with a reciprocating structured collimator unit in optical computed tomography.

FIG. 10 shows a system for computed tomography where the source or sources a, b, and c (112) produce a number of beams which converge on or near the surface of the breast to be scanned 104 and are recorded by a collimated detector or detectors a', b', and c' (110). Thus, a particular point or location is sampled from a plurality of angles. The source(s), collimator(s), and detector(s) then rotate in a discrete step and another point or location in the same plane is scanned. Additional detectors can be positioned to record scattered radiation for the plurality of angles which are sampled for each location. See, e.g., Nelson, et al., U.S. Pat. No. 4,984,974.

Several techniques for estimating the scatter content of the primary beam have been described in our previous patents. Backscattered and transmitted radiation can be evaluated for scatter content by varying the angular selectivity of the collimation associated with the exit surface point. For example, this can be accomplished by defocusing a lens system or expanding an aperture opening. In this way radiation measurements can be made which vary from weakly collimated to highly collimated radiation. Additional scatter information can be acquired by measuring scatter radiation about the location of the exit surface point. We have already discussed the use of polarized filters as collimators. Another on-axis scatter correction method is to modify the polarization of the beam between measurements and then compare the measurements. See Nelson, et al., U.S. Pat. No. 4,984,974. In this instance, because the measurements are taken at separate times, the original detector also serves the function of a second detector. If a beam splitter can be used to separate the exiting beam (transmitted and/or backscattered) into two components then two detectors can be used to make simultaneous measurements of the beam components.

Alternatively, scatter information can be obtained by juxtaposing (positioning spatially off-axis) a second parallel radiation beam of a different wavelength or other distinctive characteristic to the primary radiation beam being measured. A narrow spectral bandwidth filter which removes the primary beam but transmits the fraction of the second beam scattered into the position of the primary beam provides an estimate of scatter. If the wavelength (and other characteristics) of the second beam is the same as that of the first, then any overlap in time between the two beams should be minimized. An alternative approach in both of these cases is to simply measure the relative output signal increase when the second source is added. The collimated beam recorded at one site provides possible scatter correction values for surrounding detector sites. Instead of spatially separating the two beams, the second beam can enter at the same location as the first beam, but the second beam should be tilted (positioned angularly off-axis) with respect to the first beam. A narrow spectral bandwidth filter which reflects the second beam scattered radiation to a second detector while allowing the primary beam to reach the primary detector can provide dynamic scatter correction measurements. Of course, a single detector can be used if the two measurements can be made at different times. Transmitted radiation measurements can be made from opposite directions by positioning a source and a detector with its collimator on opposite sides of the breast, recording the transmitted radiation, reversing the positions of the source and detector with its collimator, recording the transmitted radiation, and evaluating the two measurements for differences in radiation levels and scatter content. The two measurements can also be combined to give an average measurement. As shown in FIG. 12, an acquisition format can be devised that permits both backscattered and transmitted radiation measurements to be made from both sides of the breast 104 by operating the sources 112 at slightly different times or at different wavelengths or both (other properties of the radiation such as polarization, etc. can also be used to differentiate the two sources). This allows the detectors 110 to differentiate between backscattered radiation and transmitted radiation. This configuration can be used to measure strictly backscattered or strictly transmitted radiation if desired. This "monostatic" configuration is a specific implementation of a "bistatic" configuration where sources 112 and receivers 110 need not be aligned. Bistatic configurations can be employed to record weakly collimated signals, highly collimated signals, and virtual collimated signals.

Figure 14:
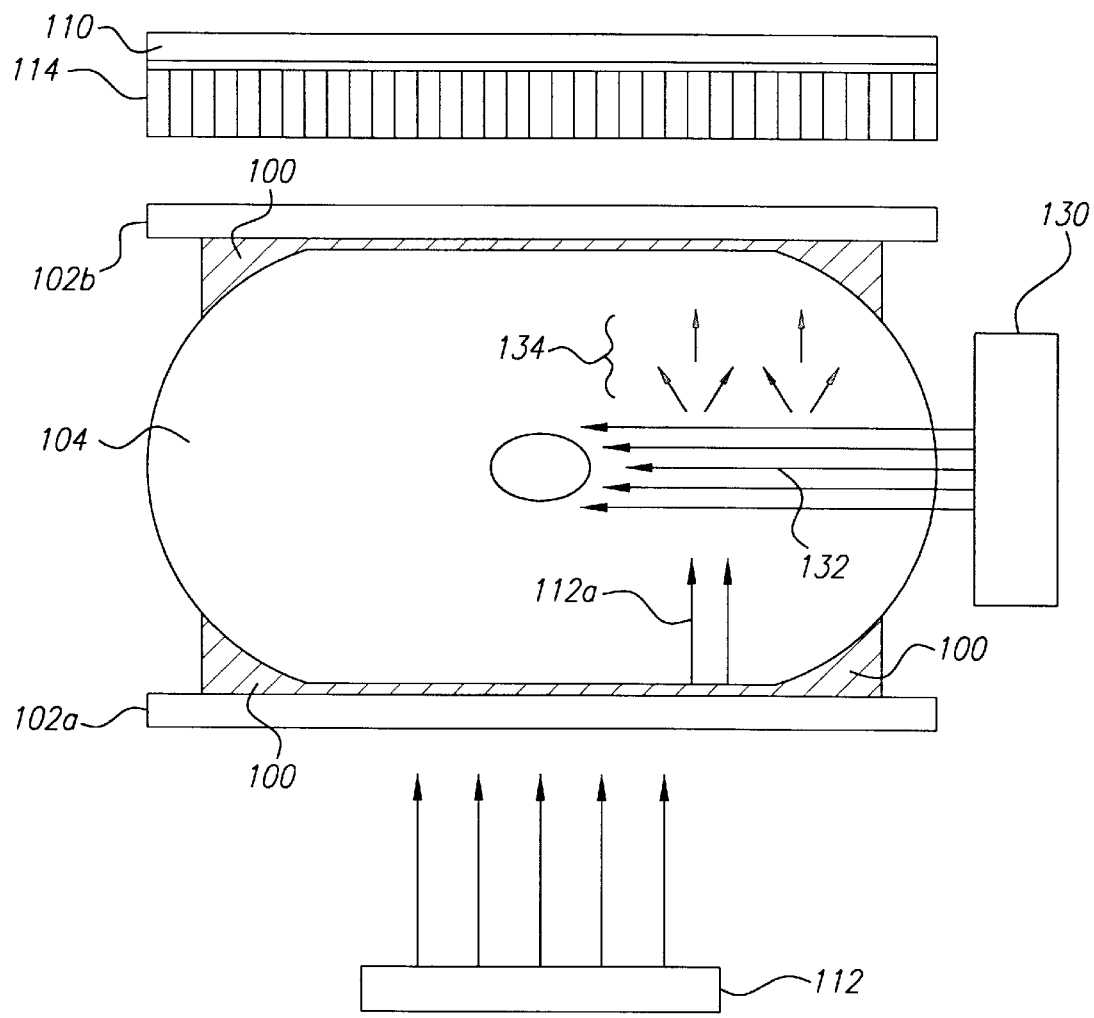
FIG. 14 shows an embodiment of an acousto-optic breast imaging device.

An acoustic source 130 can be used to create an acoustic radiation field 132 within a volume of breast tissue 104 as is generally shown in FIG. 14. The acoustic field 132 alters the optical properties of the various materials within that volume. A variety of acoustic waveforms and sources can be utilized, as is well known in geophysics, ocean acoustics, photoacoustics, and ultrasound. As is specifically shown in FIG. 14, a single acoustic source or source array 130 generates an acoustic field 132 that is intersected by an optical (radiation) beam 112a and results in a modified light field 134. The high resolution optical (radiation) scanning techniques described previously can be implemented (including the use of compression). Thus, radiation source requirements can range from continuous to pulsed. Time-resolved optical techniques can be employed for appropriate thicknesses of tissue. Optical coupling materials 100 can be used to improve transmission of radiation into and out of the breast 104, etc. The ability to distinguish between adjacent sources on the basis of their radiation properties (wavelength, polarization, etc.) allows the superposition of multiple source-mask units. This permits a much larger area to be imaged at any instant. In one implementation of this concept, the superposition of multiple patterned source inputs forms a single large area beam comprised of many discrete elements. By using an optical imaging system which offers inherent high spatial contrast resolution, spatial information can be obtained which is not necessarily limited by the acoustic wave form employed (for example, the effective acoustic pulse width).

The acoustic field can be employed with the optical tomography system described previously (Nelson, et al., 4,948,974, Aug. 14, 1990) and, therefore, with multiple discrete-angle beam optical tomosynthesis techniques. Changes in the amplitude and characteristics of the transmission and backscatter radiation, which may include the presence of Doppler-shifted (frequency-shifted) radiation, can be evaluated with the acoustic field present and not present. If the spatial extent of the acoustic radiation field is reasonably well-defined, the intersection of the optical (radiation) beam at an appropriate angle to the acoustic field provides three dimensional information since the interaction volume is approximately described by the intersection of the two fields. Thus, acousto-optic transmission and backscattered tomography is possible. As described earlier, source requirements can range from CW to rapidly pulsed. The acoustic signature of a structure or structures (influenced by factors such as geometry and material composition) within the breast can be observed, as well as the decay of the acoustic signal. Doppler-shifted radiation may be useful in identifying blood flow or structures which react with the acoustic field in a fashion which is different from that of healthy tissue.

Although FIG. 14 shows single acoustic and optical sources, more than one acoustic source and more than one optical source may be used. For example, an acoustic source directed into the plane of FIG. 12 could be added to the image acquisition system of FIG. 12. The benefits of using an acoustic field in conjunction with various collimated radiation source-detector formats can also be appreciated in an imaging system which relies on diffusive, diffusive wave or time-resolved optical techniques. In addition, appropriate collimation can be employed with diffusive, diffusive wave and timeresolved optical techniques. The use of acoustic radiation fields with optical radiation fields can aid in identification of static and dynamic structures and in identification of the material composition of the structures. The dynamics of the acoustic field can be followed by observing when optical field parameters, which may include the presence of Doppler-shifted radiation, at a given location change relative to the initiation or modulation of the acoustic field and/or relative to the optical field at a different location.

Figure 16A:
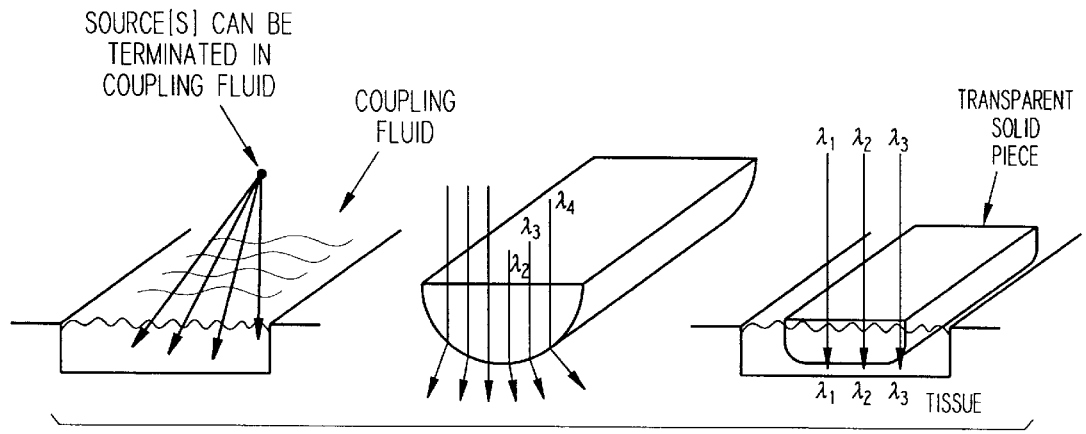
FIG. 16a shows a scanning mechanism for use with an open compression plate which provides efficient coupling of collimated radiation into the breast and additional compression.
Figure 16B:
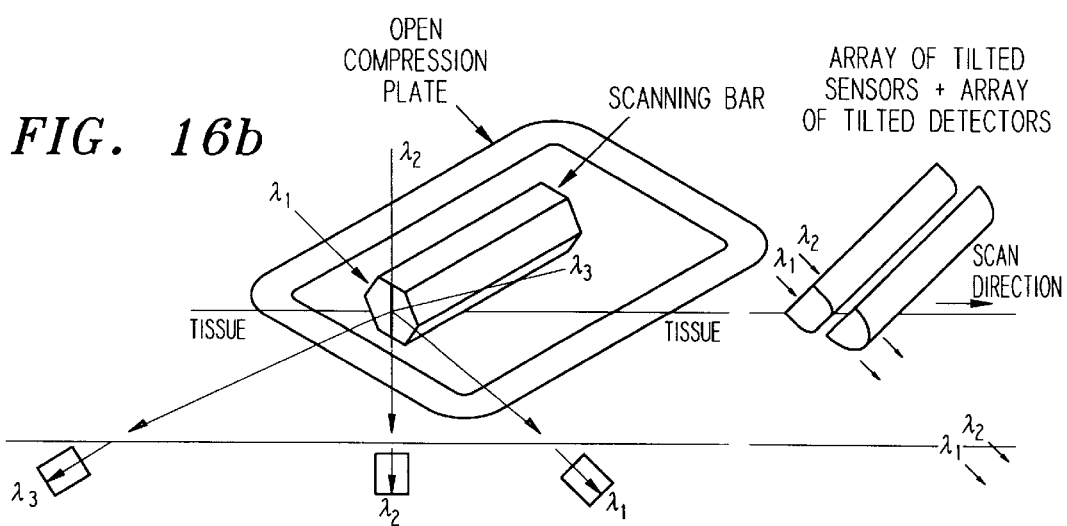
FIG. 16b shows a scanning mechanism for use with an open compression plate which provides efficient coupling of angled collimated radiation into the breast and additional compression.

The present invention also relates to enhancements to the compression plate design such that one or both compression plates have an open region adjacent the skin surface. This open region typically allows air or a coupling fluid/gel to be in contact with the skin surface. FIG. 15 shows an embodiment of an open compression plate. A coupling fluid/gel in the open area can reduce index of refraction mismatches, help provide a uniform scanning thickness, help dissipate heat buildup, and act as a lubricant for motion of the plate(s) or scanning mechanisms. FIG. 16*a* shows a scanning mechanism (which may include a source and/or detector) that moves past an open region in a compression plate while scanning and providing additional compression. If the lower compression plate also has an open region, a second similar scanning mechanism could be scanned in synchrony with the first unit, providing additional local compression. Compression plate(s) with an open region may be used to couple on-axis and off-axis (angled) collimated radiation into and out of the breast more efficiently as is shown, for example, in FIG. 16*b*. Radiation from an acoustic source can also be coupled into and out of open region(s) of compression plate(s), enabling compression acoustic image data and acoustooptic image data to be acquired as well as optical image data. Ideally, appropriate coupling fluid/gel would be used for acoustical and optical coupling. In addition, optically absorptive coatings can be used to cover parts of the plates and thereby prevent unwanted scatter from reaching the detector. An example is shown in FIG. 15. Acoustically absorptive coatings can be similarly utilized when appropriate and plates may be constructed from acoustically absorptive materials if desired.

The acoustic waveform can be readout at the exit surface (which could also be the entrance surface) by using an acoustic tranducer(s) or by using a laser to scan the breast surface or a surface coupled to the breast such as a deformable mirrored or reflective deflection plate or surface or elastic layer (such deformable mirrored deflection plates are employed in a scanning laser acoustic microscopy or SLAM). An efficient design, if optical and acoustic capabilities are designed into a single system, is to use a deformable mirrored or reflective surface which is reflective at the readout beam wavelength and transmissive for wavelengths used for optical imaging. The acoustic readout mechanism used with a bladder is not restricted to optical laser Doppler scanning vibrometry or holographic vibrometry imaging. Acoustic tranducers of various types may be coupled to the bladder as sources and/or receivers. More than one bladder unit can be used at a time and bladder units (for example, functioning as both source and receiver) need not be parallel and/or on opposite sides of the breast being imaged.

As is mentioned above, the concept of a deflection plate can be extended to include a deformable (flexible or elastic) reflective surface or layer such as a plastic sheet. The deformable layer or surface can also function as a transducer if a piezoelectric material such as a piezoceramic, a piezocomposite, or a piezopolymer such as PVDF is employed.

The combination of an open compression plate with a deflection plate or elastic layer of material across the opening can be thought of as a compression imaging bladder for optical, acousto-optical, and acoustic imaging. The rigid walls of the plate enable compression over a specific region while the deflection plate or elastic layer provides a uniform interface and good contact with the skin surface or an intermediate coupling fluid. Such a compression imaging bladder provides the same benefits that an open compression plate offers by immobilizing a region of the breast and thus limiting the effect of patient motion. The compression imaging bladder also promotes a uniform thickness of coupling fluid/gel with tissue (ensuring that gaps or discontinuous regions of the breast surface are filled) over the imaging region while minimizing motion of the fluid/gel. The elastic layer can be designed to be sufficiently pliable such that it can conform to irregular surfaces, reducing acoustic problems encountered at skin-air interfaces while providing a detection environment with predictable optical or acoustic properties.

A simple variation of this design allows a separate bladder unit (which can be referred to as an imaging bladder) to be inserted into the opening of a compression plate(s) rather than using a layer fixed to the compression plate(s). A source, a receiver, or both can be incorporated into this separate imaging bladder unit just as they could be incorporated into the compression imaging bladder. If the imaging bladder can be sealed and pressurized (expanding the bladder and providing relatively rigid walls), then compression can also be obtained by using only the imaging bladder without the compression plates. The compressive force is now applied to the frame of the imaging bladder rather than the compression plates (see FIG. 20). Thus the imaging bladder is modified into a variation of the compression imaging bladder. We shall refer to both compression imaging bladders and imaging bladders as bladders.

Several advantages of using bladder are that it can be incorporated into compression plates (e.g., in the "open" region), it can replace one or both optical compression plates, it can promote a flat region of reasonably uniform thickness like compression plates do, it promotes efficient acoustic coupling into or out of the tissue medium (including reducing the effects of an irregular surface geometry), and it can provide compression to reduce the thickness of the tissue region. It is highly desirable to have a readout environment with predictable characteristics. Both conventional acoustic transducer and optical readout techniques can be employed with a bladder(s). If an acoustic transducer is utilized, it may function as source and/or receiver. Non-medical applications which require acoustic imaging or material analysis can also benefit from the use of bladders. Bladders can improve acoustic coupling into and out of a structure, reduce effects due to adjacent boundaries of the object, fill gaps due to irregular surface geometry, and provide compression (which may reduce the thickness of the volume being scanned, help create a more-uniform interface over a region which is to be analyzed, and/or reduce object motion). A straightforward example is the use of one or more bladders (see FIG. 20) for examining small containers such as packages and envelopes using acoustics. Coupling acoustic energy into and out of such a container would be improved compared to open air coupling, unnecessary scattering/reflection from some container edges or air pockets (due to an irregular surface) could be minimized, and undesirable container motion could be controlled. A bladder may also be advantageous for both medical and non-medical imaging situations where it is desirable to have the source or readout mechanism adequately separated from the object surface. This physical separation is similar to the concept of employing an air gap (a coupling medium gap) as means of collimation. For example, when a longer TOF or when separation of interfering signals arriving from the subject is desired.

The present invention also relates to imaging breasts using multiple collimated angled beams (including normal incidence). These beams may have different characteristics and need not sample the same region at the same time. Thus, a single beam can scan a particular location from a plurality of angles in succession. Multiple beams can scan a particular location over a range of angles at the same time or at different times. As explained earlier, a single beam can be comprised of several distinct beams which are separated after exiting the breast. Off-axis radiation can be used to correct for scatter contributions to the received signal in this case (and, as is shown in FIG. 10, also in a version of CT in which radiation beams are incident at a point on the surface from a plurality of angles). This approach can be used with a compressed region of breast. A beam or beams (which may be point, line, or area type) can scan a compressed region from a plurality of angles. In addition, angled scanning can be accomplished using more than one scan direction and even complicated scan patterns can be implemented. Similar scanning techniques are employed in x-ray tomography. See, e.g., W. Merideth, et al., Fundamental Physics of Radiology, p. 351–363 (1972) and E. Christensen, et al., An Introduction to the Physics of Diagnostic Radiology, p. 249–267 (1978). Separate angled images can be formed from the data or images can be synthesized from all or part of the transmitted and/or backscattered data. Angled scans can be implemented on both sides of the subject. Since the data is in electronic form, the process of forming new images from many views can be described as optical tomosynthesis.

Tomosynthesis can be viewed as a limited implementation of CT in which the range of acquisition angles and/or the acquisition geometry have been restricted. See U.S. Pat. No. 4,767,928. In U.S. Patent No. 4,829,184 the present inventors show how to obtain three dimensional information by using transmission and backscatter imaging from opposite sides of a (preferably, compressed) breast (i.e., two views taken at 180 degree angles from each other). A third measurement taken at a 90 degree angle relative to the two views could provide additional three dimensional image information. In U.S. Pat. No. 4,948,974 we show how to obtain three dimensional information by using transmission and backscatter imaging of a (preferably, compressed) breast with a focused beam which has a well-defined depth of focus over a limited range. The focused beam can be thought of as comprising a number of beams which are incident on the breast from a plurality of angles (which need not be limited to lie in a single plane). Indeed, one or more collimated beams can be scanned across the surface of the focusing lens (or lens system) which in turn would transmit deflected (angled) scanning collimated beam(s) and, thus, simulate the geometry of a focused beam while providing more control over processing of the components of the focused beam.

With this focused beam implementation of tomosynthesis it is possible to acquire multiple image slices by scanning along a plane corresponding to each slice, adjusting the height of the beam waist, and scanning along another plane. Image resolution within a slice can be enhanced by deconvolving the overlapping information from other planes. The scanning geometry of a focused beam need not be restricted to a plane parallel to the surface. In fact, it need not be restricted to a plane at all. Complex scan geometries can be implemented, of which many are known in the field of tomographic radiography.

Optical tomosynthesis can thus be achieved using collimated radiation beams and a plurality of discrete angles of incidence. A convenient scanning arrangement involves using a focused beam as described. Scanning with a focused beam may be easier to implement while discrete angle scanning may provide better control for image reconstruction (multiple discrete images will already exist) as well as improved scatter correction capability. Discrete angle scanning may allow use of virtual collimated transmitted or backscattered radiation more effectively than if a focused beam is used. Tomosynthesis based on a focused beam or discrete multiple scanning angles can be implemented with the various waveforms described previously (Cw, pulsed, coded, complex, CW-modulated, time-resolved, etc.). For example, diffusive wave tomosynthesis can be implemented.

Figure 17:
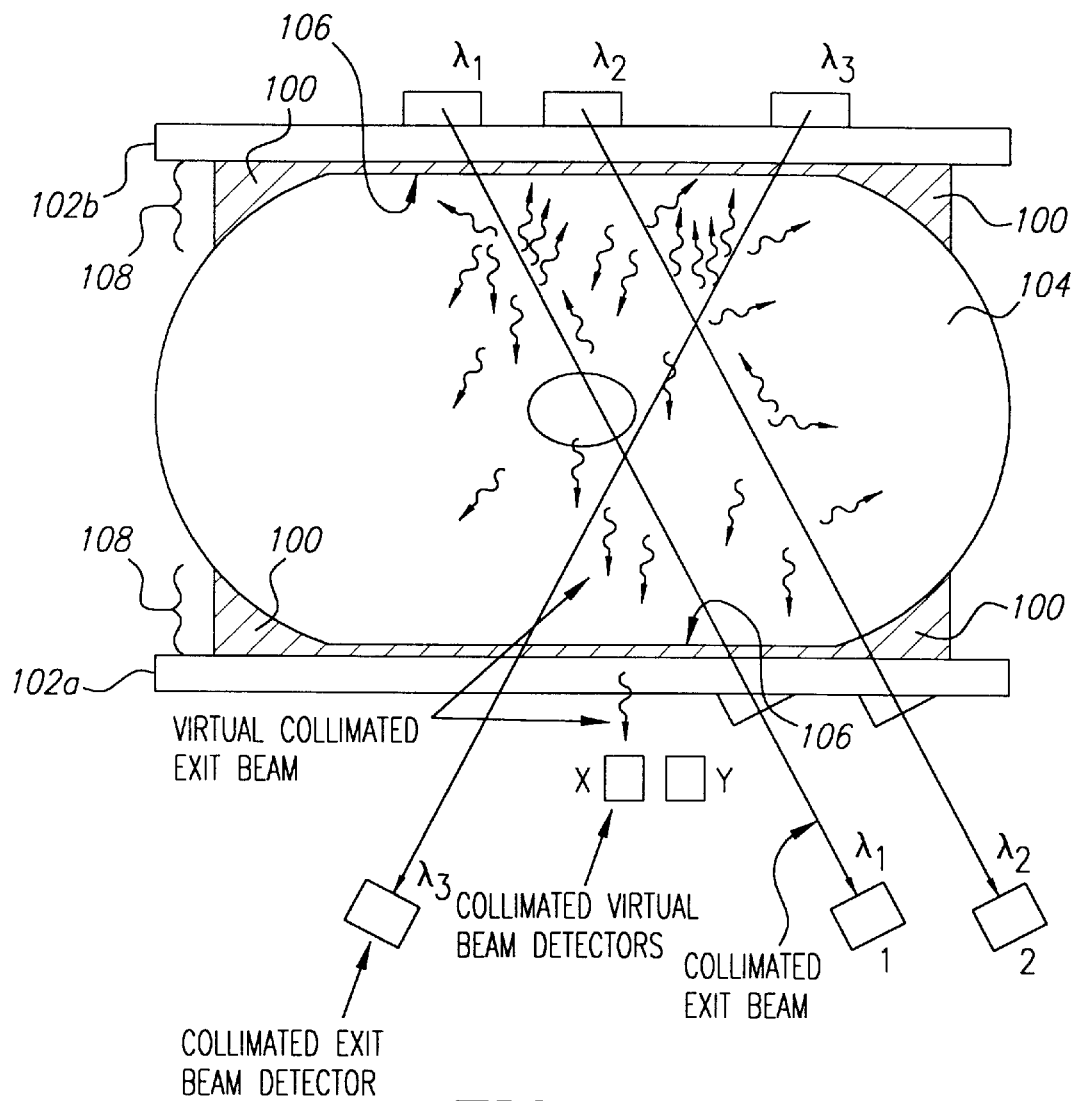
FIG. 17 shows a compressed breast with multiple collimated angled scanning beams and virtual collimated beams.

FIG. 17 shows several angled beams scanning segments of the same compressed region. If the beams have comparable characteristics (e.g., wavelength, polarization, etc.) then it may be useful to launch the beams at slightly different times so as to minimize cross-talk between them. The use of a compression plate with an open region (also referred to as an open compression plate) and an optional coupling fluid or gel provides a more uniform thickness over a region and thus would be beneficial for use with angled beam time-resolved imaging techniques. Transmitted and backscattered angled beam radiation can be collimated using previously described techniques. For example, FIG. 12 shows collimation of radiation where the angle of the incident beam is normal to the surface. A number of methods described earlier can be utilized to correct for scatter in the collimated angled beam. The use of multiple angled beams and (if appropriate) compression plates can enhance the capability of an imaging system to localize the presence of contrast-enhancing materials or materials which can be detected using emission fluorescence (including tissue-dependent fluorescence lifetimes), Raman scattering techniques, or Doppler techniques, in addition to detecting any other measurable effect such materials might have on the optical beams.

Virtual transmitted and backscattered collimated radiation beams can be generated from angled beams and can also be used for imaging and/or image enhancement. Since the source requirements can range from CW to rapidly pulsed, conventional optical collimation techniques as well as time-resolved, CW, and modulated CW (such as diffusive wave) optical imaging techniques, or optical techniques which use a coded or complex waveform can be used to evaluate the angled collimated beams and the virtual collimated beams. FIG. 17 shows an example of collimated angled beams as well as virtual collimated beams. In FIG. 17, a subset of possible virtual collimated beam directions is shown as traveling normal to the exit surface 106. These beams are shown being recorded by collimated detectors x and y. Other virtual collimated beam directions can also be evaluated.

As is described previously, optical tomosynthesis can be accomplished using a focused beam and is equivalent to scanning using a plurality of angled collimated beams. See Nelson, et al., U.S. Pat. No. 4,984,974 and above. A focused detector can be employed in order to implement virtual tomosynthesis by using a plurality of virtual collimated angled beams. Such virtual collimated beams may be useful since they appear to originate below the skin surface of the breast being imaged. A source which appears to originate within the breast (i.e. below the skin surface) can illuminate a region (via transmission or backscatter) from a different perspective than traditional projection. See Nelson et al., U.S. Pat. No. 4,829,184. Thus, three-dimensional image information can be synthesized using data acquired from multiple projections. This information could include data from the multiple collimated angled beams (transmitted and backscattered) or the multiple virtual collimated beams or the multiple collimated angled beams in conjunction with the virtual collimated beams. Virtual collimated beam data can also be acquired while implementing optical CT imaging, providing virtual collimated transmission and backscatter CT images. The virtual collimated beam data can also be used to enhance the collimated beam CT images.

Figure 18:
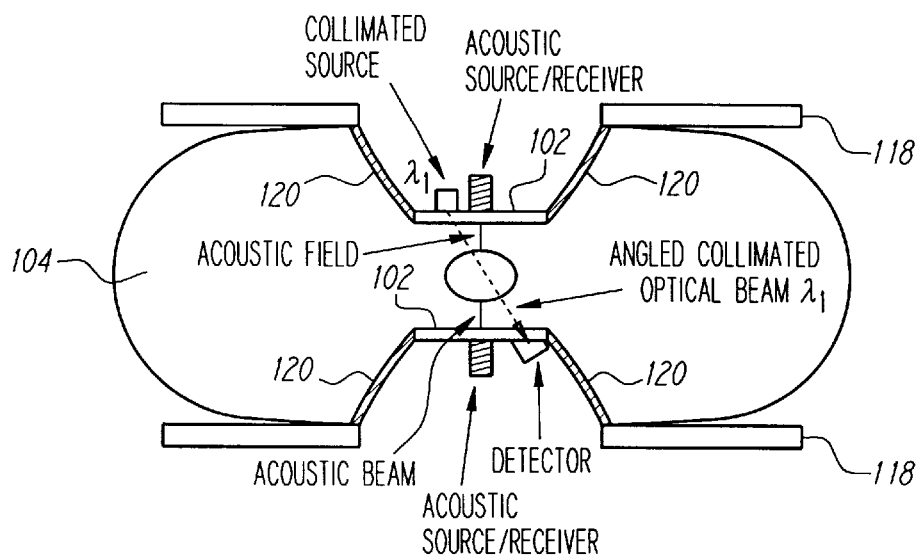
FIG. 18 shows an open contoured compression plate used in an acousto-optic imaging system. The collimated angled optical beam is shown interacting with a focused acoustic beam. Each of the two acoustic units may be used as a source and/or receiver.

The present invention also relates to acquiring additional information about tissue characteristics by intersecting an acoustic field with an optical radiation field. We have already described how the use of one or more acoustic radiation fields can be used to modify collimated transmitted or backscatter optical radiation beams. This approach can now be extended to collimated angled optical radiation beams and virtual collimated transmitted and backscattered radiation beams as just described. The dynamics of the acoustic field can be monitored with one or more collimated angled optical beams. In addition, the use of an open compression plate(s) creates a more favorable environment for incorporating an acoustic source(s) into the same scanning geometry employed for the optical source(s), as shown in FIG. 18. In this case the optical coupling material should also be appropriate for coupling the acoustic source to the breast. The acoustic beam can enter the breast at normal incidence or be tilted with respect to the surface. The acoustic beam can be focused (collimated) with an acoustic lens or by the technique of electronic beam forming (also referred to as electronic collimation) which is widely used in medical ultrasound. Although the acoustic source is typically used as a receiver for backscattered radiation, additional acoustic receivers can be used to measure the transmission beam and virtual transmission and backscattered acoustic radiation beams. This is the acoustic analog of imaging with optical virtual collimated beams. The concepts of raster scanning with a focused acoustic source and using off-axis scattered acoustic radiation are well known in the field of industrial ultrasound imaging (e.g., bistatic imaging, Synthetic Aperture Focusing Techniques). See J. Krautkramer, et al., Ultrasonic Testing of Materials (1990).

We need not be limited to using acoustic transducer arrays as sources and receivers as is now widely practiced in medical ultrasound imaging. An acoustic lens assembly or unit can be used with a transducer to scan the breast in a raster mode with a collimated (focused) acoustic beam (a method which we described previously using optical radiation sources). Also see Christensen, et al., An Introduction to the Physics of Diagnostic Radiology, p. 249–267 (1978). It is also possible to scan the breast with a number of focused acoustic beams either by using a combination of multiple sources with multiple lens units or a collimated acoustic source with a mask (in a manner similar to the corresponding optical technique shown in FIG. 2). This acoustic raster scan technique can also be implemented without an intersecting optical radiation field. A collimated acoustic receiver (which can also be a source) can be used to detect the exiting acoustic radiation field. Another approach which we have already described is to use a laser beam of appropriate wavelength to detect the effects of the acoustic field by various vibrometry techniques such as scanning (or by using holographic imaging) the breast surface or a surface coupled to the breast surface. These acoustic data acquisition techniques are now widely used in industry. Two such methods are C-mode and Scanning Laser Acoustic Microscopy, also referred to as C-SAM and SLAM, and laser vibrometry. See L. Santangelo, et al., Surface Mount Technology (September 1989); and Proceedings, SPIE vol. 2358 Conference on Vibration Measurements by Laser Techniques: Advances and Applications (1994). A compression plate can be modified to include a readout surface similar to the deformable mirrored deflection plate used with SLAM systems. As we is also previously described, the open compression plate in conjunction with a deformable mirrored deflection plate, an elastic mirrored layer or surface, a layer, sheet, or surface which is acoustically transmissive, a sheet, layer, or surface of material which functions as an acoustic source or detector (a piezoelectric material), or an insertable bladder mechanism function as bladder.

Figure 19:
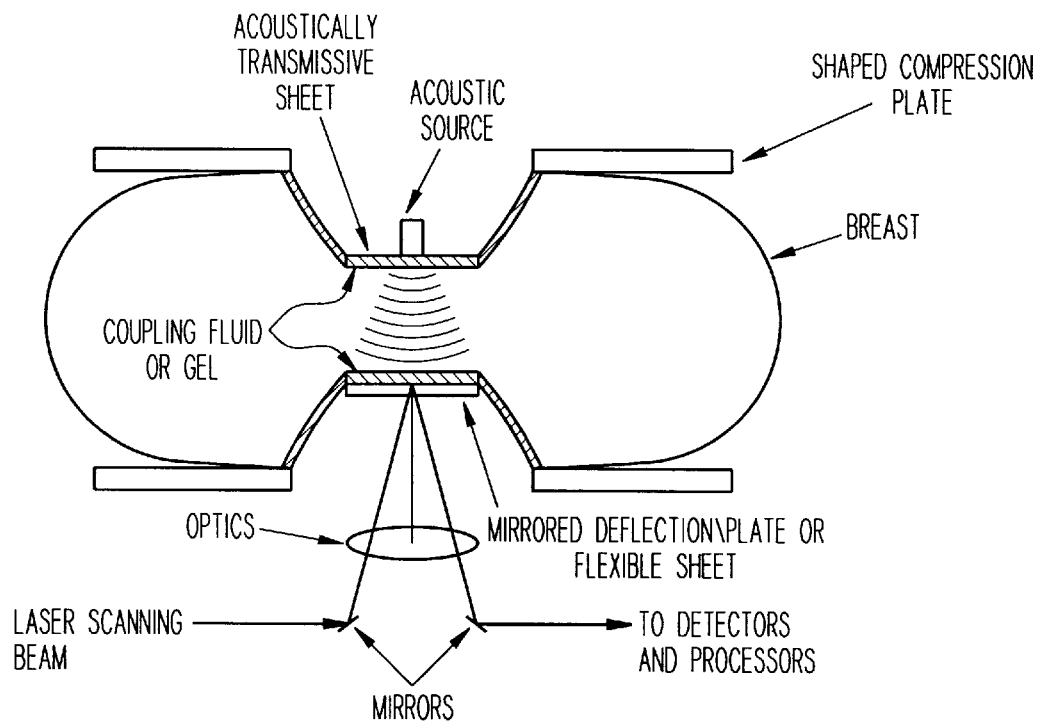
FIG. 19 shows an open contoured compression plate used with an acoustic imaging system. The transmitted beam from an acoustic source is shown passing through an acoustically transmissive layer and coupling material and into the breast. The exiting acoustic field distorts the deformable mirrored or reflective surface of a deflection plate or elastic layer or sheet which is scanned by a laser beam to detect the acoustic pattern. The incorporation of an acoustically transmissive layer and a mirrored deflection plate or elastic layer with shaped compression plates are examples of compression imaging bladders (or simply bladders).

FIG. 19 shows two shaped compression plates with openings which have been modified to function as bladders for imaging and tissue characterization. The lower bladder employs an optical readout while the upper bladder incorporates an acoustically-transmissive layer which couples the transducer to the breast while presenting a smooth surface to the transducer. Here the transducer could operate as both a source and a receiver. A variation on this idea is to have both bladders provide source-receiver capabilities. It is also possible to work with a single bladder unit. An alternative design is to configure the source unit and the readout unit as bladder modules which would simply be inserted into the open compression plates. The bladder modules would be attached directly to the compression plates or an external force (such as a mechanical arm, a human hand, liquid or air pressure, gravity, etc.) would be used to press the elastic acoustically-transmissive layer of the bladder module against the breast surface and thus ensure good coupling of radiation into or out of the breast.

FIG. 20 shows a bladder device inserted into the opening of a shaped compression plate. The deformable layer or surface can be particularly useful when placed at locations on the breast surface where the boundaries have steep slopes such that the breast surface in the opening of the compression plate(s) presented depressions instead of being relatively uniform. We have discussed this problem earlier with respect to TOF applications where the use of a coupling liquid or gel was proposed to ensure that the scanned beam of optical pulses required approximately the same travel time when scanning a surface with an irregular geometry. The elastic layer and any coupling fluid or gel it contains can extend the breast volume, reducing problems caused by radiation reflecting from a skin-air interface. Offering a bladder module as an option may be more cost effective for users who only require compression plates for breast imaging.

In general, acoustic transmission and backscatter compression data can be acquired as well as acoustooptic compression data. Thus, acoustic, optic, and acousto-optic information can be acquired and evaluated independently and also compared to form a more complete characterization of the breast tissue being imaged. The use of compression with ultrasound will improve the efficacy of ultrasound mammography imaging. The region being scanned tends to be of a more uniform thickness and the typical penetration depth for ultrasound radiation used in mammography is now more appropriate for the thickness of tissue (making transmission ultrasound mammography a viable imaging technique).

Just as optical tomosynthesis is possible from multiple collimated (focused) angled optical (radiation) beams, so acoustical tomosynthesis (synthetic aperture imaging) is possible from multiple collimated (focused) angled acoustic beams. The collimated acoustic beams can be electronically or mechanically scanned through a range of angles and the acoustic source (and receiver) can be scanned or translated in the same manner as the optical source (and receiver).

Several acoustic sources may be used together to set up complex propagating wavefronts, standing wavefront patterns, or compensated wavefronts (such as time reversal mirrors) which could improve imaging and tissue identification. See SPIE vol. 1733 (F. Lizzi, ed., 1992). In addition, virtual collimated (focused) acoustic radiation beams can be measured along with the transmitted and/or backscattered collimated acoustic beams with the aid of additional collimated (acoustic lens, physical separation, electronic beam forming, TOF, acoustic holography) acoustic receivers. A variety of acoustic waveforms can be employed and acoustic source requirements may range from CW to pulsed. Coherent acoustic imaging techniques which use TOF principles, beam forming (phased array), and synthetic aperture methods are commonly used in medical ultrasound, industrial acoustics, and underwater acoustics. See Modern Acoustical Imaging (H. Lee & G. Wade, eds. 1986). Synthetic aperture methods are also widely used in radar imaging. See D. Wehner, High Resolution Radar (1987); and M. Soumekh, Fourier Array Imaging (1994). Types of acoustic sources include single transducer probes, line arrays, two-dimensional arrays, focused tranducers, and focused tranducer arrays. Optoacoustic sources (such as pulsed, and possibly scanning, laser beams) can also be used if advantageous (although focusing may require beam forming or making use of a short pulse duration). Both static and dynamic (Doppler) acoustic imaging should benefit from the use of compression. See Christensen, et al., An Introduction to the Physics of Diagnostic Radiology, p. 249–267 (1978); and W. Hedrick, et al., Ultrasound Physics and Instrumentation (1995).

The present invention also relates to imaging using compression plates, with or without an open area, in conjunction with weakly collimated sources and receivers. For example, an optical fiber or waveguide used to collect non-ionizing radiation can be designed with a large acceptance angle. Compression can be used with conventional diffuse and diffusive wave electromagnetic or diffractive (refractive) acoustic or acousto-optic imaging techniques. See, e.g., A. Kak, et al., Principles of Computerized Tomographic Imaging (1988); and Image Recovery Theory and Application (H. Stark ed. 1987). Compression reduces the tissue volume (and propagation distances) which is considered and provides a controlled (predictable) geometry. Thus, introducing compression can be very beneficial when attempting to reconstruct the properties of a tissue volume.

Imaging will involve the use of one or more sources and one or more receivers. A receiver or array of receivers can be used on both sides of the compressed region for recording the diffusive or diffusive wave signal from individual sources. Sources can be also be used on both sides of the compressed region. The present inventors presented a similar technique in U.S. Pat. No. 4,829,184, and in pending U.S. patent application Ser. No. 08/480,760, the disclosures of both of which are hereby incorporated by reference as if fully set forth herein, in which the scattered field is measured in the immediate region surrounding the collimated source or detector. In the presently described technique the sources and receivers are weakly collimated and the receivers are used to sample the scatter field over an appropriate area. Sampling densities and uniformity are influenced by a number of parameters including the wavelength of the radiation, thickness of tissue, tissue composition, limits on acquisition time, reconstruction algorithms employed, equipment costs, etc. Similar choices should be made for the tomosynthesis imaging techniques described earlier.

Data from multiple sources can be acquired at the same time or at distinctly separate times depending on how the specific contribution of each source can be recognized by a detector(s). Sources can be perceived as being distinct if they are spatially well-separated, or are active at different times, or have different wavelengths or polarizations (in the optical case), etc. As an example, in an optical case a source can be a combination of two or more distinct wavelengths. The wavelengths are separated at the receiver and the information evaluated for each wavelength. In addition, the information can be combined and/or compared. For example, wavelength-dependent phase shifts or relative attenuation can be considered. An intermediate implementation of this invention is to acquire collimated data (collimated source and collimated receiver) as well as diffuse data from the collimated source. Yet another implementation is to acquire collimated data using a collimated source and separately acquire the diffusive or diffusive wave data using weakly collimated sources and receivers. Thus, additional information will be available for image reconstruction and data fusion. In addition to the pulsed, continuous, and modulated waveforms that can be provided by a source, complex and coded waveforms may also be employed.

The acoustic, optic, and acousto-optic apparati and methods we have described may also be used for non-medical applications such as inspection of containers, monitoring industrial processes, materials analysis, defect analysis, etc.

Though the invention has been described with respect to specific preferred embodiments thereof, many variations and modifications will immediately become apparent to those skilled in the art. It is therefore the intention that the appended claims be interpreted as broadly as possible in view of the prior art to include all such variations and modifications.

We claim:

1. A mammography imaging apparatus using non-ionizing radiation comprising:
    at least one source of non-ionizing radiation of relatively narrow spectral bandwidth disposed such that the radiation from said at least one source will be incident on a portion of the breast to be scanned,
    at least one radiation detector disposed so as to detect radiation having passed through the portion of the breast to be scanned,
    a collimator corresponding to each detector and adapted to be disposed between the portion of the breast to be scanned and each detector,
    a radiation imager for translating said detected radiation into a mammography image, and
    a structure for enabling shaping at least a region of the breast and for providing compression to the breast, said structure being positionable adjacent the breast, and said structure having at least one open region enabling access to a surface of the breast, the surface of the breast accessible through said at least at least one open region substantially defining a plane wherein the structure is configured to provide compression to the breast in a direction substantially perpendicular to said plane of the surface of the breast accessible through said at least one open region.

2. The apparatus of claim 1 wherein said at least one source of non-ionizing radiation of relatively narrow spectral bandwidth is disposed such that the radiation from said at least one source will be incident over a plurality of angles on the portion of the breast to be scanned.

3. The apparatus of claim 2 further comprising
    at least one additional source of non-ionizing radiation disposed such that the radiation from said additional source is incident over a plurality of angles of the portion of the breast to be scanned,
    at least one additional detector corresponding to and disposed to detect radiation from the at least one additional source after said radiation exits the portion of the breast, and at least one additional collimator corresponding to each additional detector and adapted to be disposed between the portion of the breast to be scanned and said corresponding additional detector.

4. The apparatus of claim 3 wherein the at least one additional source is a source of acoustic radiation.

5. The apparatus of claim 4 wherein the at least one additional detector corresponding to the acoustical radiation source is at least one of a deformable mirrored deflection plate, a reflective elastic layer, and a bladder.

6. The apparatus of claim 4 wherein the at least one additional detector corresponding to the acoustical radiation source is a bladder comprising a structure for shaping at least a region of the breast and for providing compression to the breast.

7. The apparatus of claim 1 wherein the at least one source comprises at least one of an optical radiation source and an acoustical radiation source.

8. The apparatus of claim 1 wherein said at least one source comprises an acoustical radiation source emitting acoustical radiation, said acoustical radiation detectable by at least one detector comprising at least one of a deformable mirrored deflection plate, a reflective elastic layer, and a bladder.

9. The apparatus of claim 8 wherein said at least one detector comprises a bladder configured to detect acoustical radiation exiting the portion of the breast, said bladder positionable adjacent the breast.

10. The apparatus of claim 9 wherein said bladder includes an acoustic transducer.

11. The apparatus of claim 9 wherein the bladder comprises at least one of a deformable mirrored deflection plate and a reflective elastic layer.

12. The apparatus of claim 9 wherein the bladder comprises a structure for shaping at least a region of the breast and for providing compression to the breast.

13. The apparatus of claim 1 wherein the structure comprises two plates of substantially the same size.

14. The apparatus of claim 13 wherein the two plates can be moved in tandem along the breast to be scanned during image acquisition.

15. The apparatus of claim 1 wherein the structure comprises two plates of different sizes.

16. The apparatus of claim 15 wherein at least one plate can be moved during image acquisition.

17. The apparatus of claim 16 wherein the structure is contoured and provides at least one of gradual compression to the breast, a flat radiation entrance surface, and steep compression to the breast.

18. The apparatus of claim 1 wherein the apparatus is configured such that said at least one source of non-ionizing radiation of relatively narrow spectral bandwidth is disposed such that the radiation from said at least one source will be incident on a portion of the breast to be scanned having a volume less than a volume of the entire breast.

19. The apparatus of claim 1 wherein the structure for enabling shaping at least a region of the breast and for providing compression to the breast is substantially transparent to non-ionizing radiation.

20. The apparatus of claim 1 wherein the structure is contoured and provides at least one of gradual compression to the breast, a flat radiation entrance surface, and steep compression to the breast.

21. A method for obtaining mammography images of a portion of the breast using non-ionizing radiation comprising the steps of:

(1) positioning a structure for enabling shaping at least a region of the breast and for providing compression to the breast proximate to the breast to be scanned, said structure having at least one open region enabling access to a surface of the breast the surface of the breast accessible through said at least one open region substantially defining a plane;

(2) compressing the breast with the structure in a direction substantially perpendicular to said plane the surface of the breast accessible through said at least one open region;

(3) irradiating the portion of the breast with non-ionizing radiation of a relatively narrow spectral bandwidth, said radiation incident on the portion of the breast at a plurality of angles;

(4) allowing the radiation to transmit through the portion of the breast;

(5) collimating the radiation;

(6) detecting at least one of transmitted radiation, backscattered radiation, virtual collimated transmitted radiation, virtual collimated backscattered radiation, radiation due to emission fluorescence, radiation due to Raman scattering, and radiation due to Doppler scattering with a radiation detector; and (7) translating the detected radiation into a mammography image of the portion of the breast.

22. The method of claim 21 wherein the step of irradiating the portion of the breast with non-ionizing radiation of a relatively narrow spectral bandwidth comprises (1) positioning at least one source of non-ionizing radiation of relatively narrow spectral bandwidth proximate the surface of the breast accessible through said at least one open region in said structure; and (2) irradiating the portion of the breast with non-ionizing radiation of a relatively narrow spectral bandwidth from the source.

23. The method of claim 21 including the additional step of introducing a coupling material of suitable index of refraction between the source of non-ionizing radiation and the surface of the breast.

24. The method of claim 21 wherein the optically transparent structure comprises two plates of substantially the same size, the method including the additional step of moving the two plates of the optically transparent structure in tandem simultaneously with irradiating the portion of the breast.

25. The method of claim 21 wherein the optically transparent structure comprises two plates of substantially different size, including the additional step of moving at least one plate of the optically transparent structure simultaneously with irradiating the portion of the breast.

26. The method of claim 21 wherein the portion of the breast imaged has a volume less than a volume of the whole breast.

27. The method of claim 21 wherein steps 1–7 are repeated for a plurality of portions of the breast to be scanned.

28. The method of claim 27 including the additional step of combining the mammography image formed for each portion of the breast to be imaged into a complete image of the breast.

29. The method of claim 21 wherein the structure comprises a contoured compression plate and the step of compressing the breast provides at least one of gradual compression to the breast, a flat radiation entrance surface, and steep compression of the breast.

* * * * *

UNITED STATES PATENT AND TRADEMARK OFFICE
CERTIFICATE OF CORRECTION

PATENT NO. : 5,999,836
DATED : December 7, 1999
INVENTOR(S) : Robert S. Nelson et al.

It is certified that error appears in the above-identified patent and that said Letters Patent is hereby corrected as shown below:

Title page,
In the Reference Cited, please add the following,
OTHER PUBLICATIONS Nagasawa, C., Abo, M., Yamamoto, H., and Uchino, O., "Random Modulation CW Lidar Using New Random Sequence", *Applied Optics*, Vol. 29, No. 10, April 1, 1990, pp. 1466-1470

Rubenstein, E., Hughes, E.B., Campbell, L.E., Hofstadter, R., Kirk, R.L., Krolicki, T.J., Stone, J.P., Wilson, S., Zeman, H.D., Brody, W.R., Macovski, A., and Thompson, A.C., "Synchrotron Radiation and Its Application to Digital Subtraction Angiography", *SPIE*, Vol. 314 Digital Radiography (1981), pp. 42-49

Scwentner, N., N., Hahn, U., Einfeld, D., and Muhlhaupt, G., "Time Resolved Spectroscopy with Synchrotron Radiation". *Nuclear Instruments and Methods*, 167 (1979), pp. 499-503

Llacer, J., "Preliminary Study of a Germanium Three-Dimensional Camera for Positron Emitting Radioisotopes", *IEEE Trans. Nucl. Sci.*, NS-20, No. 1 (1973), pp. 282-293

Jacobs, A.M., Towe, B.C., and Harkness, J.E., "Backscatter X-Ray Radiography: Medical Applications:, *SPIE*, Vol. 206, *Recent and Future Developments in Medical Imaging II* (1979), pp. 129-134

Battista, M.SC., Santon, L.W., Eng, B., and Bronskill, M.J., Ph.D., "Compton Scatter Imaging of Transverse Sections: Corrections for Multiple Scatter and Attenuations", *Phys. Med., Biol.*, 1977, Vol. 22, No. 2, pp. 229-244

Liu, J., Nishimura, D., and Macovski, A., "Generalized Tomosynthesis for Focusing on an Arbitrary Surface", *IEEE Transactions on Medical Imaging*, Vol. 8, No. 2, June 1989, pps. 168-172

Johns, P.C., and Yaffe, M.J., "Coherent Scatter in Diagnostic Radiology", *Medical Physics* 10(1), Jan./Feb. 1983, pp. 40-50

UNITED STATES PATENT AND TRADEMARK OFFICE
CERTIFICATE OF CORRECTION

PATENT NO. : 5,999,836
DATED : December 7, 1999
INVENTOR(S) : Robert S. Nelson et al.

It is certified that error appears in the above-identified patent and that said Letters Patent is hereby corrected as shown below:

Nishimura, D.G., Macovski, A., and Brody, W.R., "Digital Tomosynthesis Using a Scanned Projection Radiographic System", *SPIE*, Vol. 314, *Digital Radiography* (1981), pp. 31-36

*Radiological Health Handbook*, Bureau of Radiological Health, U.S. Dept. of Health, Education and Welfare, Public Health Service, Food and Drug Administration, (Jan. 1970), pp. 133 and 437-438

Sappey, A.D., "Optical Imaging Through Turbid Media with a Degenerate Four Wave Mixing Correlation Time Gate", *Applied Optics*, Vol. 33, No. 36, Dec. 20, 1994, pp. 8346-8354

Santangelo, L.J., and Kessler, J.W., "Acoustic Microscopy: A Key Inspection Tool for Improving the Reliabilty of Surface Mount Capacitors and Plastic IC Packages," *Surface Mount Technology*, Setp. 1989 (5 pages)

Johnson, C.C., "Optical Diffusion in Blood", *IEEE Transactions on Bio-Medical Engineering*, Vol. BME-17, No. 2, Apr. 1970, pp. 129-133

Pedersen, G.D., McCormick, N.J., and Reynolds, L.O., "Transport Calculations for Light Scattering in Blood:, *Biophysical Journal*, Vol. 16, 1976, pp. 199-207

Marks, F.A., Tomlinson, H.W., and Brooksby, G.W., "A Comprehensive Approach to Breast Cancer Detection Using Light: Photon Localization by Ultrasound Modulation and Tissue Characterization by Spectral Discriminaton", *SPIE*, Vol. 1888 (1993), pp. 500-510

Duguay, M.A., and Mattick, A.T., "Ultrahigh Speed Photography of Piosecond Light Pulses and Echos", *Applied Optics*, Vol. 10, No. 9, Sept. 1971, pps. 2162-2170

UNITED STATES PATENT AND TRADEMARK OFFICE
CERTIFICATE OF CORRECTION

PATENT NO. : 5,999,836
DATED : December 7, 1999
INVENTOR(S) : Robert S. Nelson et al.

It is certified that error appears in the above-identified patent and that said Letters Patent is hereby corrected as shown below:

Column 12,
Line 57-58, please change "region (s)" to -- region(s) --.

Column 20,
Line 65, please change "timeresolved" to -- time-resolved --.

Column 21,
Line 29, please change "acoustooptic" to -- acousto-optic --.

Column 24,
Line 11, please change "(Cw" to -- (CW --.

Column 26,
Line 48, please change "acoustooptic" to -- acousto-optic --.

Column 27,
Line 22, please change "Optoacoustic" to -- Acousto-optic --.

Column 28,
Line 51, please change "plane wherein" to -- plane, wherein --.

Column 30,
Line 3, please change "breast the" to -- breast, the --.
Line 7, please change "plane the" to -- plane of the --.

Signed and Sealed this

Twenty-fifth Day of December, 2001

Attest:

Attesting Officer

JAMES E. ROGAN
Director of the United States Patent and Trademark Office